US011092610B2

(12) United States Patent
Lee et al.

(10) Patent No.: US 11,092,610 B2
(45) Date of Patent: Aug. 17, 2021

(54) BIOMARKER SBP1 FOR EARLY DIAGNOSIS OF KIDNEY DISEASES, AND USE THEREOF

(71) Applicant: CELLGENTEK CO., LTD., Daejeon (KR)

(72) Inventors: Byung Mu Lee, Gyeonggi-do (KR); Hyung Sik Kim, Gyeonggi-do (KR); Kyeong Seok Kim, Gyeonggi-do (KR); Ji Yeon Son, Gyeonggi-do (KR)

(73) Assignee: CELLGENTEK CO., LTD.

( * ) Notice: Subject to any disclaimer, the term of this patent is extended or adjusted under 35 U.S.C. 154(b) by 14 days.

(21) Appl. No.: 16/327,905

(22) PCT Filed: Aug. 16, 2017

(86) PCT No.: PCT/KR2017/008911
§ 371 (c)(1),
(2) Date: Feb. 25, 2019

(87) PCT Pub. No.: WO2018/038452
PCT Pub. Date: Mar. 1, 2018

(65) Prior Publication Data
US 2019/0277859 A1    Sep. 12, 2019

(30) Foreign Application Priority Data

Aug. 26, 2016   (KR) .................. 10-2016-0109119
May 17, 2017    (KR) .................. 10-2017-0061144

(51) Int. Cl.
G01N 33/53      (2006.01)
G01N 33/68      (2006.01)
C12Q 1/68       (2018.01)

(52) U.S. Cl.
CPC ........... *G01N 33/6893* (2013.01); *C12Q 1/68* (2013.01); *G01N 33/68* (2013.01); *G01N 2800/347* (2013.01)

(58) Field of Classification Search
None
See application file for complete search history.

(56) References Cited

U.S. PATENT DOCUMENTS

| 7,879,548   | B2 * | 2/2011  | Tsuang ................ | C12Q 1/6883 435/6.16 |
| 2008/0261218 | A1   | 10/2008 | Tsuang et al.         |                      |
| 2010/0190652 | A1 * | 7/2010  | Nagalla ............... | G01N 33/6893 506/7  |
| 2010/0240546 | A1 * | 9/2010  | Lo .................... | G01N 33/57423 506/9 |
| 2011/0287964 | A1 * | 11/2011 | Bonventre ............. | G01N 33/6893 506/9  |

FOREIGN PATENT DOCUMENTS

| JP | 2009-511028 A    | 3/2009  |
| KR | 10-2010-0035637 A | 4/2010  |
| KR | 10-2015-0041375 A | 4/2015  |
| KR | 10-1576586 B1    | 12/2015 |

OTHER PUBLICATIONS

Stammer et al., Selenim-Binding Protein 1 expression in ovaries and ovarian tumors in the laying hen, a spontaneous model of human ovarian cancer, Gynecologic Oncology 109, 2008, pp. 115-121. (Year: 2008).*
Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, pp. 1-7. (Year: 2014).*
Bellomo et al., Acute kidney injury, Lancet vol. 380, Aug. 25, 2012, pp. 756-766. (Year: 2012).*
Strongin, Laboratory Diagnosis of Viral Infections, Sensitivity, Specificity, and Predictive Value of Diagnostic Tests: Definitions and Clinical applications, Lennette, ed. Marcel Dekker, Inc. New York, pp. 211-219, 1992. (Year: 1992).*
Ha et al., Decreased selenium-binding protein 1 mRNA expression is associated with poor pronosis in renal cell carcinoma, World Journal of Surgical Oncology 2014, 12:288, pp. 1-7. (Year: 2014).*
Son et al., "New Biomarkers for Early Detection of Heavy Metal-induced kidney Injury," The Korean Society of Environmental Health and Toxicology, 2014 Spring Conference Abstracts, May 2014, p. 465.
Wang et al., "New urinary biomarkers for diabetic kidney disease," Biomarker Research, 2013, vol. 1, No. 9, internal pp. 1-4.

* cited by examiner

*Primary Examiner* — Gary Counts
(74) *Attorney, Agent, or Firm* — Riverside Law LLP

(57) ABSTRACT

A biomarker and a technology for utilizing the same, of the present invention, can be useful in the early diagnosis, in urine, of a renal function abnormality due to diabetes and drugs and in the prediction and evaluation of disease severity, and, further, can accurately determine, with high sensitivity and specificity, a renal function abnormality due to diabetes and exposure to drugs, and enable the early and effective diagnosis of kidney abnormality symptoms through a relatively simple method, thereby being widely usable in various fields, such as in clinical experiments essential for new drug development and in diagnosing drug-causing acute/chronic renal failure, which can frequently occur in the clinical treatment process.

3 Claims, 35 Drawing Sheets
Specification includes a Sequence Listing.

BIOMARKER SBP1 FOR EARLY DIAGNOSIS OF KIDNEY DISEASES, AND USE THEREOF

CROSS-REFERENCE TO RELATED APPLICATIONS

This application is the U.S. national phase application filed under 35 U.S.C. § 371 claiming benefit to International Patent Application No. PCT/KR2017/008911, filed on Aug. 16, 2017, which is entitled to priority under to Korean Patent Application No. 10-2016-0109119, filed Aug. 26, 2016 and Korean Patent Application No. 10-2017-0061144, filed May 17, 2017, the disclosure of which is incorporated herein by reference in its entirety.

TECHNICAL FIELD

The present invention relates to a biomarker for early diagnosis of a kidney disease, which is Selenium-Binding Protein 1 (SBP1), and a use thereof. More particularly, the present invention relates to a composition for detecting a biomarker for early diagnosis of a kidney disease, a kit including the same, an animal test method and a clinical trial method using the same, and a detection method thereof.

BACKGROUND ART

The kidney is an organ that excretes various materials metabolized in the body and thus present in the blood, and particularly, an organ that filtrates the blood through glomerular filtration, and renal tubular absorption and resorption, thereby excreting unnecessary wastes in the body in the form of urine. The kidney weight is only approximately 0.5% of a body weight, but the amount of blood flowing to the kidney is 20 to 25% of the total cardiac output. Therefore, the kidney is one of the most vulnerable organs due to a variety of toxic xenobiotics in the blood. For example, when an excessive drug is injected into the body, or various types of metabolic diseases such as heart disease, diabetes and high blood pressure occur, the kidney may be very slowly injured, and renal function is finally stopped without subjective symptoms, such that toxic xenobiotics are not excreted to the outside of the body, leading to additional complications.

Particularly, acute/chronic kidney diseases caused by diabetes and drugs are cases frequently occurring in clinical practice. It is known that 10-20% of the cases of acute deterioration of renal function are caused by drugs, and also acute renal failure frequently occurs in patients who underwent organ transplantation such as heart transplantation. Currently, despite rapid advances in disease diagnosis and treatment technology, for intensive care unit (ICU) patients, acute renal failure mortality has remained approximately 50% without a great increase over the last 50 years, and this still remains a scientific challenge to overcome.

In addition, a pathological phenomenon in which kidney damage lasts 3 months or longer is called chronic kidney disease (CKD), and an increase in CKD incidence is increasing by 10% or more every year around the world including Korea, due to the emergence of the aging society and the spread of a western lifestyle. Particularly, since CKD is an irreversible disease, there are no subjective symptoms until 60% or more of the renal function is lost, but after that, in most of the patients, CKD progresses to the end-stage renal disease (ESRD), which means that they cannot lead an ordinary life without dialysis. Moreover, it is very important to diagnose CKD early because it is highly related to the occurrence of complications such as cardiovascular/cerebrovascular diseases. The prevalence of CKD is approximately 10% or more around the world, and CKD is a very common disease like diabetes or high blood pressure. In the case of Korea, it has been reported that CKD and ESRD have increased to affect one out of 10 people.

While diabetes (approximately 70% or more) has been known as the most major cause of CKD, the key mechanism of ESRD progression due to diabetic nephropathy is not clear. Recently, because of westernized eating habits and aging, the incidence of diabetes has rapidly increased, and the incidence of diabetic chronic renal failure is exponentially increasing around the world as the diabetic incidence increases.

At present, in Korea, one in every 10 people is counted as suffering from diabetes, and in the elderly over 60 years, two in every 10 people have diabetes, and another two in every 10 people have impaired glucose tolerance, which is the pre-stage of diabetes. Considering the current trends, it is expected that the incidence of diabetes will increase explosively in the next 10 to 20 years. In the United States, medical costs for the treatment of diabetic patients has reached 44 billion dollars annually, accounting for the largest portion of single diseases, and including indirect costs, enormous economic losses of 98 billion dollars or more may result annually. Therefore, the prevention of the occurrence and progression of complications caused by diabetes is a very important issue in a socioeconomic aspect such as reduction of medical expenses, as well as reduction of incidence and mortality of the patients.

Diabetes is complicated by vascular complications, rather than the disease itself, and diabetic nephropathy, which is one of the diabetes-induced vascular complications, is the No. 1 cause of ESRD. In Korea, it has been reported that the number of diabetes-induced ESRD patients is continuously increasing, and diabetic nephropathy accounts for 47.1% of all causes of ESRD. Therefore, according to this trend, it is expected that the number of ESRD patients will increase due to the increase in diabetic nephropathy, and thereby, there is a concern that the reduction of life quality and economic burden of a patient with a kidney disease due to dialysis, organ transplantation, etc. will increase. In recent years, in the United States, as the incidence of diabetic nephropathy has been reported to increase by nearly two-fold, resulting in enormous medical burdens, diabetic nephropathy has received public health attention.

Diabetic nephropathy is divided into four stages according to a glomerular filtration rate and proteinuria, and in the stages of diabetic nephropathy, it can be seen that microalbuminuria precedes the decrease of a glomerular filtration rate. In addition, at the beginning of diabetic microalbuminuria occurring in stage 2, anatomical changes already begin in the kidney. However, in the case of microalbuminuria, there is a limit because specificity is low for the diagnosis of diabetic renal failure. That is, in the United States, among 7 million diabetic nephropathy patients, nearly 2 million patients do not have microalbuminuria, and therefore, there is a limit to diagnosis of diabetic nephropathy using microalbuminuria.

Given the steady increase in diabetic nephropathy, currently used general treatment including a diet, exercise and pharmacotherapy is not appropriate, and various approaches to the cause of the disease, other than conventional methods of treating diabetes and diabetic nephropathy, are needed. At present, to prevent diabetes-induced nephropathy, a renin-angiotensin system (RAS) inhibitor has been used, but treatment with the RAS inhibitor slows down the progression to chronic renal failure, but cannot achieve complete prevention. Therefore, it is imperative to establish new indicators for early diagnosis and progression of diabetic nephropathy, and determination of therapeutic effects on diabetic nephropathy.

The currently-known risk factors associated with the progression of diabetic nephropathy include increased age, longer duration of diabetes, the rapid decline of GFR, pronounced glomerular damage, high HbA1c, hyperlipidemia (cholesterol, triglyceride), high blood pressure, the presence of diabetic neuropathy, the presence of diabetic retinopathy, a positive family history, an increased body weight or waist-to-hip ratio, and smoking, and with the management of these risk factors, efforts are being made for diagnosis of diabetic nephropathy. When a diabetic kidney disease is diagnosed, annual monitoring of GFR on regular basis is important to assess progression of impairment of renal functions, and at the same time, the tracking of changes in microalbuminuria is performed.

Clinically, since GFR reflects more accurate renal functions than changes in microalbuminuria, the change of GFR is an important factor that determines the prognosis of a patient. According to several clinical trials conducted for both type I and II diabetic patients, and particularly, patients with CDK at stage 3 or higher, a urine protein level reduced after initial treatment is considered a good indicator reflecting the prognosis of the kidney, but for patients with CDK at stages 1 and 2, which are the early stages of a kidney disease, it is known that the early reduction in urine protein after treatment is not a long-term prognostic factor of the kidney.

It is estimated that most diabetic patients have a large amount of proteinuria, but it was reported that approximately 30 to 40% of patients have deteriorated renal function without microalbuminuria. According to recent studies on the prevalence of patients deteriorated in renal function without proteinuria, among the patients with type II diabetes, the frequency of patients having a GFR of less than 60 mL/min/1.73 m$^2$ was 23.1%, which is approximately 1.3-fold higher than those of normal persons, and 55% of the diabetic patients with deteriorated renal function did not have microalbuminuria.

Several hypotheses have been suggested as the causes of diabetic patients with deteriorated renal function without microalbuminuria. First, it is estimated that the deteriorated renal function without microalbuminuria results from a combination of the possibility of the loss of proteinuria due to an effect of a RAS inhibitor used in most patients, regulation of blood pressure by using a blood pressure regulating drug and an effect of a hyperlipidemia drug, the possibility in which diabetic complications mainly occur in tubular interstitial tissue and a non-diabetic kidney disease concomitant with diabetes is accompanied, diseases in renal vessels invading the afferent arteriole and the rapid progression of the aging process of the kidney. However, since there is currently no study on the pathophysiologic mechanism for patients with diabetic nephropathy without microalbuminuria, a more aggressive study of the pathophysiology and treatment of diabetic CKD not concomitant with proteinuria is needed, and since renal function may be reduced without microalbuminuria in patients diagnosed with diabetes, it is necessary to establish early indicators for evaluating kidney injury.

Particularly, due to diabetic CKD, a patient spends 1.8-fold more on medical costs, and when dialysis progresses, the burden increases to 10.3-fold, resulting in a huge medical burden caused by diabetic diseases and the aging society (Park et al., 2014). As of the end of 2013, approximately 80,000 Koreans cannot live a healthy life without receiving renal replacement therapy, which results in a great burden on individuals and the society. Particularly, hemodialysis is performed at least three times a week, and the cost of dialysis is very high. For example, a single session of dialysis costs at least 160,000 won, and medical expenses of approximately 2,500,000 won or higher is required per month. 90% of the medical expenses are paid by the National Health Insurance, and thus a huge government medical budget is needed (one trillion won per year).

Since it is difficult to diagnose CKD because of no specific symptoms, and the disease progresses for a long time and gives a risk to life, prevention of the progression of kidney injury by early detection of CKD and initiation of treatment at an appropriate time may be the most effective way to prevent CKD and various complications concomitant therewith.

Meanwhile, the diagnosis of CKD is usually performed by functional evaluation of the kidney. That is, CKD is diagnosed by general indicators such as GFR estimation using serum creatinine and proteinuria quantification, but since these indicators are changed after the kidney injury is in advanced stages, it is impossible to normally repair the injured kidney after diagnosis, and creatinine, which is used as the most important indicator, is changed according to age, sex, muscle mass, thyroid function, a diet pattern and medication, and thus has a limitation as a factor for accurate measurement and prediction of renal function.

Meanwhile, as it has been reported that acute kidney injury (AKI) is closely associated with GFR reduction and patient mortality, a movement for estimating kidney injury by developing indicators for assessing kidney injury is actively progressing. Studies on replacement of pre-existing renal function indicators (serum creatinine and BUN) reflected at the end stage of kidney injury due to deterioration in renal function are growing.

Novel kidney injury biomarkers that have been internationally suggested include kidney injury molecule-1 (KIM-1), neutrophil gelatinase-associated lipocalin (NGAL) and beta2-microalbumin, and various clinical trials are being conducted to examine whether KIM-1, NGAL, N-acetyl-D-glucosaminidase (NAG), urinary non-albumin protein (uNAP) and heart-type fatty acid binding protein (H-FABP) can be used as biomarkers for a kidney disease.

Biomarker-related studies performed for diabetic patients revealed that there are significant relationships between NGAL and GFR and between uNAP and albuminuria, and the relationship between these novel biomarkers and kidney injury has been identified. However, most of the studies had only a small cross-sectional study population. Therefore, time-dependent predictive changes of the novel biomarkers and diabetic kidney injury cannot be accurately reflected, and the diagnostic power of the existing biomarkers has been evaluated as not being superior to that of microalbuminuria. Although studies on the clinical applicability of these biomarkers have been accelerated, they have not been commercialized yet due to the relevance to a disease-specific kidney injury mechanism, the lack of evaluation of predictive power in clinical samples, etc. Particularly, since the new biomarkers have not been applied to diabetic kidney injury yet, and in fact, non-specific proteinuria or microalbuminuria and serum creatinine are used, early diagnosis is difficult.

The inventors constructed a cross-sectional study/follow-up patient group with diabetic nephropathy to deduce a novel biomarker based on a proteome and evaluate clinical applicability, and in addition, the effectiveness and predictive power of the newly-discovered kidney injury biomarker were verified, and the validity of the verified effects was proved by comparing the newly-discovered kidney injury biomarker with the previously-suggested kidney injury biomarkers.

In the cases of acute/chronic renal failures, after the occurrence of symptoms, the progress of a disease should be determined on a time basis, and therefore early diagnosis and early treatment are very important to determine future life prognosis, but there are no diagnostic markers thereof yet. To cope with this problem, recently, various types of kidney disease biomarkers have been developed and used, but all of the biomarkers in blood should be used, and the diagnosis of renal failure has been conventionally performed with an increase in serum creatinine (SCr) as an indicator. However, in fact, when renal impairment occurs, serum Cr increases after a considerable progression of renal dysfunction, and thus at the time of diagnosis of acute/chronic renal failure, the optimal timing to treat the renal dysfunction is often missed. For this reason, serum Cr is insufficient as a diagnostic marker for acute/chronic renal failure, and it is imperative to discover an early biomarker using urine (refer to Korean Unexamined Patent Application Publication No. 10-2010-0035637).

DISCLOSURE

Technical Problem

The present invention is suggested to solve the conventional technical problems described above, and the inventors had attempted to develop a method for early diagnosis of a diabetic kidney disease with higher sensitivity and specificity than the previously used markers for determining a kidney disease, such as serum Cr and blood urine nitrogen (BUN), and confirmed that a concentration of Selenium-Binding Protein 1 (SBP1) released into urine according to a disease condition is measured using technology using an antibody, thereby determining a kidney disease with high specificity and sensitivity at the early stage of renal failure. As a result, the present invention was completed.

Therefore, the present invention is directed to providing a composition for early diagnosis of a kidney disease, which includes an agent for measuring SBP1 in urine.

The present invention is also directed to providing a kit for early diagnosis of a kidney disease, which includes the composition.

The present invention is also directed to providing a method for detecting SBP1 in a sample (urine) of a subject to provide information required for diagnosis of a kidney disease.

However, technical problems to be solved in the present invention are not limited to the above-described problems, and other problems which are not described herein will be fully understood by those of ordinary skill in the art from the following descriptions.

Technical Solution

In one aspect, the present invention provides a composition for evaluating early diagnosis of a kidney disease, which includes an agent for measuring an expression level of SBP1.

In one exemplary embodiment of the present invention, the SBP1 may consist of an amino acid sequence of SEQ ID NO: 1.

In another exemplary embodiment of the present invention, the agent for measuring an expression level of the SBP1 may be an antibody specific to SBP1 in urine.

In another aspect, the present invention provides a kit for early diagnosis of a kidney disease, which includes the composition.

In still another exemplary embodiment of the present invention, the kit may be a protein chip kit.

In still another aspect, the present invention provides a method for detecting SBP1 in a sample of a subject to provide information required for diagnosis of a kidney disease.

In yet another exemplary embodiment of the present invention, the method may further include detecting the protein or mRNA encoding the same and comparing an expression level thereof with an expression level of a corresponding protein or mRNA encoding the same in a normal control sample, and detection of the protein may be performed by an antigen-antibody reaction using an antibody specific to the corresponding protein.

In yet another exemplary embodiment of the present invention, the kidney disease may be nephrotic syndrome, kidney cancer, chronic renal failure, acute pyelonephritis, acute renal failure, hypertensive renal disease, Reye's syndrome, gout, Sjogren's syndrome, Bechet's disease, lupus, candidiasis, nephrotic hemorrhagic fever, leptospirosis, legionellosis, autosomal dominant polycystic kidney disease or hydronephrosis.

In yet another exemplary embodiment of the present invention, the kidney disease may be a diabetic kidney disease, and in this case, it is obvious to those in the art that diabetic renal failure is included in the diabetic kidney disease.

In yet another aspect, the present invention provides a method for early diagnosis of a kidney disease, which includes: (a) obtaining urine from a subject; (b) detecting SBP1 in the obtained urine using an antibody specific to SBP1; and (c) diagnosing a kidney disease when SBP1 is detected in the urine.

In yet another aspect, the present invention provides a use of an agent for measuring an expression level of SBP1 in urine for early diagnosis of a kidney disease.

Advantageous Effects

Since urinary SBP1 and a technology for utilizing the same according to the present invention can be effectively used in early diagnosis of renal dysfunction due to diabetes and a drug and prediction and evaluation of disease severity, accurately determine renal dysfunction caused by exposure to a drug with high sensitivity and specificity, and effectively diagnose abnormal symptoms in the kidney at an early stage through a relatively simple method, SBP1 is expected to be widely used in various fields such as diagnosis of drug-induced acute renal failure which can frequently occur in clinical treatment, and a preclinical toxicity test which is essential for the development of a new drug.

DESCRIPTION OF DRAWINGS

FIG. 2A shows a result of a glucose tolerance test, and FIG. 2B shows a result of an insulin sensitization test.

As shown in FIG. 3A, it was proved that a urine volume is increased in a diabetic animal, and thereby nephrotoxicity indicators such as BUN and creatinine are increased. In addition, histopathologic findings of the kidney showed that severe cell death occurs in glomeruli and renal tubules of the kidney in a diabetic animal, and as shown in FIG. 3B, it can be seen that kidney tissue was not damaged in an anti-diabetic drug-administered experimental group similar to a control.

BEST MODE OF THE INVENTION

Figure 1A:
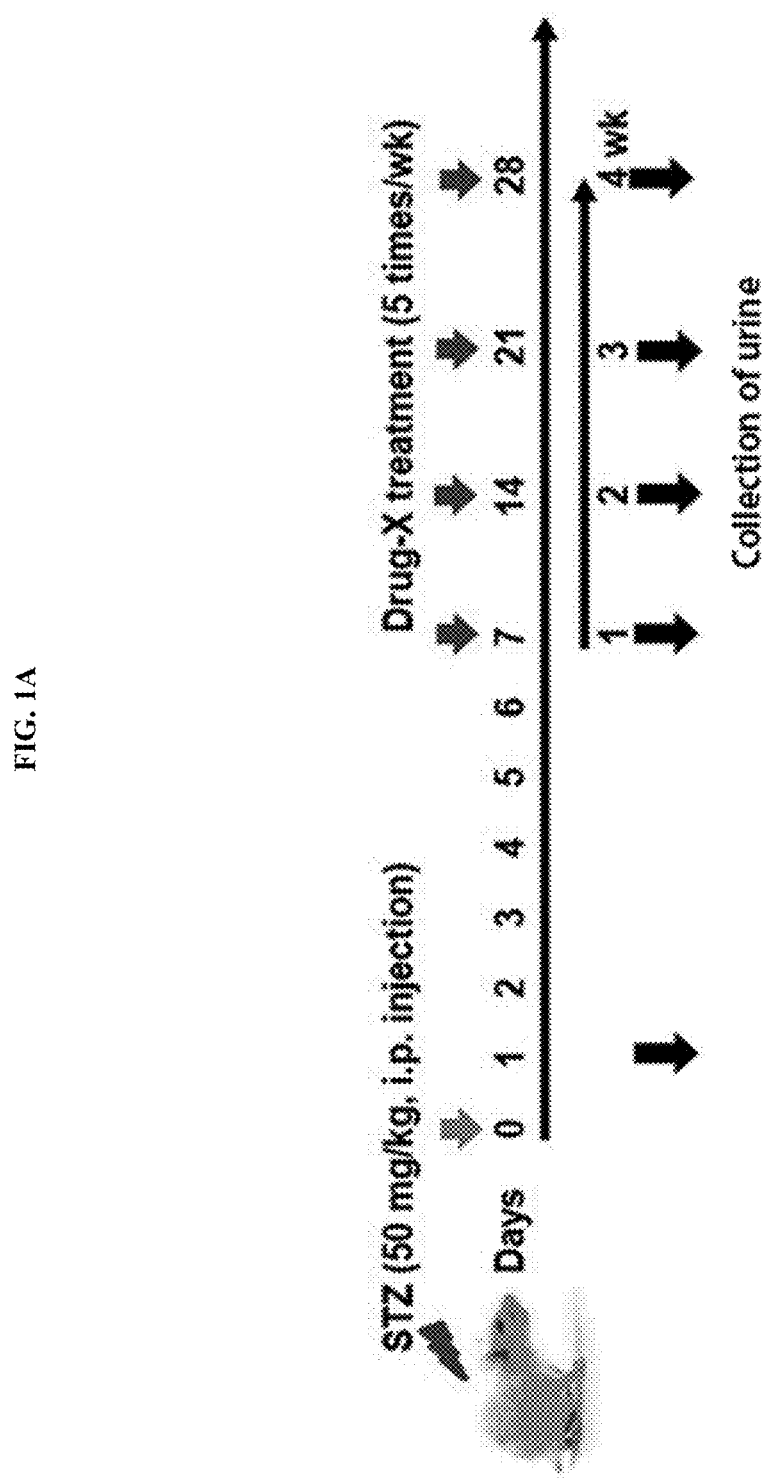
FIGS. 1A and 1B show experimental designs for establishing diabetic animal models, similar to humans, by treating streptozocin (STZ)

The inventors fully proved that renal failure caused by diabetes is induced using an animal model inducing diabetic renal failure according to exemplary embodiments, and then confirmed that SBP1 is detected in urine, and as a result of proving that SBP1 is not detected after administration of an anti-diabetic drug, the present invention was completed. In addition, as a result of measuring SBP1 in the urine of a diabetic patient, it is proved that SBP1 in urine is highly detected according to longer diabetic duration, demonstrating that SBP1 is of value as an early diagnostic marker for diabetic renal failure.

In addition, after cisplatin (CDDP), which is a drug well known as causing renal dysfunction even in an acute nephrotoxicity model, was injected into a rat, changes in SBP level contained in urine obtained for 24 hours or serum collected after autopsy from rats in an experimental group and an untreated control group were confirmed. Therefore, the present invention was completed.

In one exemplary embodiment of the present invention, to confirm the availability of SBP1 as an early diagnostic biomarker for a kidney disease, evaluation was performed by inducing renal dysfunction caused by cisplatin/$HgCl_2$, showing that serum creatinine (SCr), BUN, glucose contained in urine, LDH, aspartate aminotransferase (AST) and total protein levels are raised in the cisplatin/$HgCl_2$-administered experimental group (see Example 2).

Therefore, SBP1 according to the present invention, as a novel biomarker, can be used for various purposes and applications requiring technologies for rapid, simple and early prediction or diagnosis of the risk of renal dysfunction caused by environmental contaminants or drugs and side effects thereof from urine, instead of blood.

Hereinafter, the present invention will be described in detail.

The present invention provides a composition for early diagnosis of a kidney disease, which includes an agent for measuring an expression level of SBP1, and an amino acid sequence of the SBP1 is represented by SEQ ID NO: 1.

In the present invention, the drug includes all materials present in nature, which cause dysfunction in the kidney of an individual. For example, the drug may be, but is not limited to, cisplatin, 4-aminophenol (PAP), aristolochic acid, 2-bromoethylamine (BEA), DCVC, cadmium, cadmium chloride, cefoperazone, cephalothin, cerium nitrate, cinnabar, cyclospotine, sirolimus, doxorubicin, herba cistanches, hexachlorobutadiene, hydrocortisone, gentamicin, lithium chloride, lanthanum nitrate, nanocopper, mercuric chloride, melamine, cyanuric acid, ochratoxin A, propyleneimine, puromycin, D-serine, sodium chromate, tacrolimus, TCTFP, tobramycin, uranylnitrate, or vancomycin.

In the present invention, a heavy metal may be, but is not limited to, mercury (Hg), cadmium (Cd), platinum (Pt), lead (Pb) or chromium (Cr).

Other materials causing renal dysfunction may include, but are not limited to, halogenated hydrocarbons (e.g., carbon tetrachloride, chloroform, etc.), various types of environmental contaminants (2,4,5-trichlorophenacetic acid, the herbicide Paraquat, polychlorobiphenyls, 2,3,7,8-tetrachlorodibenzo-p-dioxin, etc.).

The term "evaluation" used herein refers to confirmation of the presence or characteristic of a pathological condition. For the purpose of the present invention, the evaluation may mean diagnosis, prediction, detection or confirmation of the occurrence and possibility of renal dysfunction.

The term "marker for evaluation, marker to be evaluated or evaluation marker" used herein refers to a material capable of distinguishing cells or tissue with renal dysfunction or probability thereof from normal cells or tissue, and includes organic biomolecules such as polypeptides or nucleic acids (e.g., mRNA, etc.), proteins, lipids, glycolipids, glycoproteins or sugars (monosaccharides, disaccharides, oligosaccharides, etc.), which are increased or reduced in renal dysfunction cells or tissue, compared with normal cells or tissue. For the purpose of the present invention, the renal function evaluation marker of the present invention is SBP1 showing a specifically high expression level in cells of tissue exposed to a renal dysfunction-causing material, compared with cells of normal kidney tissue, and showing a specifically high expression level in cells of tissue exposed to a renal dysfunction-causing material.

Information of a protein or gene of a biomarker for evaluating a kidney disease provided by the present invention may be easily obtained from a known gene database. For example, an amino acid sequence of the biomarker protein or a base sequence of mRNA encoding the same is registered in the known gene database, the National Center for Biotechnology Information (NCBI).

The term "agent for measuring a protein expression level" used herein refers to a molecule capable of being used in detection of a marker by confirming an expression level of a biomarker changed in expression by renal dysfunction as described above.

An expression level of the corresponding biomarker may be determined by confirming an expression level of a marker protein or an expression level of mRNA of a gene encoding the same.

The term "measurement of an expression level of a protein" used herein is a process of confirming the presence and expression level of a renal dysfunction marker protein in a biological sample of a subject to evaluate renal function, for example, an amount of a protein by detection of an antigen-antibody complex using an antibody specifically binding to the corresponding marker protein. Examples of specific analysis methods include, but are not limited to, western blotting, enzyme linked immunosorbent assay (ELISA), radioimmunoassay (RIA), radioimmunodiffusion, Ouchterlony immunodiffusion, Rocket immunoelectrophoresis, histoimmunostaining, immunoprecipitation assay, complement fixation assay, FACS, and a protein chip.

Preferably, the agent for measuring a protein level is an antibody.

The term "antibody" used herein, as a known term used in the art, refers to a specific protein molecule directed against an antigenic domain. For the purpose of the present invention, the antibody refers to an antibody specifically binding to the biomarker protein of the present invention, and such an antibody may be prepared, according to a conventional method, from a protein encoded by the marker gene, obtained by cloning of each gene in an expression vector according to a conventional method. Here, the antibody also includes a partial peptide capable of being made from the protein, and the partial peptide of the present invention includes at least 7 amino acids, preferably, 9 amino acids, and more preferably, 12 or more amino acids.

The type of the antibody of the present invention is not particularly limited, and the antibody includes all immunoglobulin antibodies, as well as a polyclonal antibody, a monoclonal antibody or a part thereof as long as it has an antigen-binding capability. Further, the antibody of the present invention includes a specific antibody such as a humanized antibody.

The antibody used in detection of a marker for evaluating renal function of the present invention includes a complete form having two full-length light chains and two full-length heavy chains, and a functional fragment of an antibody molecule. The functional fragment of the antibody molecule means a fragment having at least an antigen-binding function, and includes Fab, F(ab'), F(ab') 2 and Fv.

The term "measurement of an mRNA expression level" used herein is a process of confirming the presence and the degree of expression of a gene encoding a renal dysfunction marker protein in a biological sample of a subject to evaluate renal function, and may be determined by, for example, measuring an mRNA level. Specific examples of analysis methods may include, but are not limited to, RT-PCR, competitive RT-PCR, real-time RT-PCR, RNase protection assay (RPA), northern blotting and DNA chips.

An agent for measuring an mRNA expression level may be a primer pair, probes or antisense oligonucleotides. Since the nucleic acid sequence of the biomarker of the present invention has been known, primers, probes or antisense oligonucleotides, which specifically bind to a specific region of the gene, may be designed by those of ordinary skill in the art, based on the sequence.

The term "primer" used herein refers to a short nucleic acid sequence having a free 3' hydroxyl group, and specifically, a short nucleic acid sequence which forms a base pair with a complementary template and serves as a starting point for replication of a template strand. Primers may initiate DNA synthesis in a suitable buffer at a suitable temperature in the presence of a reagent for a polymerization reaction (i.e., DNA polymerase or reverse transcriptase) and four different nucleoside triphosphates. Preferably, in the present invention, PCR amplification is performed using a polynucleotide specifically binding to mRNA encoding a marker protein and sense and antisense primers so that renal dysfunction is evaluated through the production of a desired product. PCR conditions, and lengths of the sense and antisense primers may be modified based on what is known in the art.

The term "probe" used herein refers to a fragment of a nucleic acid such as RNA or DNA including several to several hundred bases, which can achieve specific binding to mRNA, and is labeled, thereby confirming the presence or absence of specific mRNA. The probe may be manufactured in the form of an oligonucleotide probe, a single-stranded DNA probe, a double-stranded DNA probe, or an RNA probe. In the present invention, renal dysfunction may be evaluated through hybridization using the marker mRNA polynucleotide and a complementary probe. Selection of suitable probes and hybridization conditions may be modified based on what is known in the art.

The primers or probes of the present invention may be chemically synthesized by a phosphoramidite solid support method or other widely-known methods. In addition, such nucleic acid sequences may be modified using various means known in the art. Non-limiting examples of such modifications include methylation, capping, substitution with one or more homologues of a natural nucleotide, and modifications between nucleotides, for example, an uncharged linker (e.g., methyl phosphonate, phosphotriester, phosphoramidate or carbamate) or a charged linker (e.g., phosphorothioate or phosphorodithioate).

The term "antisense oligonucleotide" used herein refers to a nucleic acid-based molecule which has a complementary sequence to an mRNA sequence of a targeted biomarker gene, and can form a dimer with mRNA of the marker gene.

Here, the complementary binding means sufficiently complementary binding to selectively hybridize an antisense oligonucleotide with an mRNA target of an RORC gene under predetermined hybridization or annealing conditions, and preferably, physiological conditions, and preferably, substantially complementary and perfectly complementary binding, and more preferably, perfectly complementary binding.

In addition, the present invention provides a kit for diagnosing a kidney disease, which includes an agent for measuring an expression level of SBP1 or mRNA encoding the same.

The kit of the present invention may detect a marker by confirming an expression level of a protein of a marker for evaluating renal function or a gene encoding the same. The kit for diagnosing a kidney disease according to the present invention may include a composition solution or device consisting of one or more components suitable for an analysis method, as well as primers, probes or antibodies selectively recognizing a marker to measure an expression level of the marker for evaluating renal function.

As a specific example, a kit for measuring an expression level of a marker protein for evaluating renal function according to the present invention may include a substrate, a proper buffer, a secondary antibody labeled with a chromogenic enzyme or fluorescent material, and a chromogenic substrate for immunological detection of an antibody. Here, the substrate may be a nitrocellulose membrane, a 96-well plate synthesized of a polyvinyl resin, a 96-well plate synthesized of a polystyrene resin and a slide glass made of glass, the chromogenic enzyme may be a peroxidase or an alkaline phosphatase, the fluorescent material may be FITC or RITC, and the chromogenic substrate solution may be 2,2'-azino-bis-(3-ethylbenzothiazoline-6-sulfonic acid) (ABTS), o-phenylenediamine (OPD), or tetramethyl benzidine (TMB).

As another specific example, in the present invention, a kit for measuring an expression level of mRNA of a corresponding marker may be a kit including necessary components for performing RT-PCR. The RT-PCR kit may include a test tube or different suitable container, reaction buffers (various pHs and magnesium concentrations), deoxyribonucleotides (dNTPs), enzymes such as taq-polymerase and reverse transcriptase, a DNase, an RNase inhibitor, DEPC-water, and sterile water, as well as a marker gene-specific primer pair, which is designed by those of ordinary skill in the art. In addition, the RT-PCR kit may include a primer pair specific to a quantitative control. In addition, the kit of the present invention may be a kit for detecting a marker for evaluating renal function, which includes essential components required for DNA chips. The DNA chip kit may include a substrate to which cDNA corresponding to a gene or a fragment thereof is attached as a probe, and the substrate may include cDNA corresponding to a quantitative control gene or a fragment thereof.

In addition, the present invention provides a method of detecting SBP1 or mRNA encoding the same in a sample of a subject to provide information required for diagnosing a kidney disease.

More specifically, gene expression may be detected at an mRNA or protein level, and the isolation of mRNA or a protein from a biological sample may be performed using a known process.

The term "subject" used herein refers to an animal having a kidney among all body organs, among organisms present in the nature, preferably, a mammal, and more preferably, a human. The mammal may include a rodent (a rat, a mouse, etc.), a rabbit, a horse, a cow, sheep, a dog, a cat, a monkey and a human, but a type of the subject of the present invention is not limited to the above-described examples.

The term "sample of a subject" used herein includes samples such as tissue, cells, whole blood, serum, plasma, saliva, sputum, cerebrospinal fluid or urine, in which expression levels of a marker protein for evaluating renal function or mRNA encoding the same are different, but the present invention is not limited thereto. Preferably, the sample may be renal tissue or cells constituting the same.

Through the above-mentioned detection methods, whether renal dysfunction actually occurs in a patient suspected of having a kidney disease may be confirmed or predicted by comparing a gene expression level in a normal control with a gene expression level in a subject suspected of having a kidney disease. In other words, when, by comparing an expression level of the marker of the present invention measured in a sample of cells or tissue of a subject suspected of having renal dysfunction with an expression level of the marker of the present invention measured in a sample of normal cells or tissue, it is confirmed that the expression level of the marker of the present invention in a sample derived from cells of a subject suspected of having renal dysfunction is significantly higher than that derived from normal cells, the subject can be predicted as a kidney disease patient.

Analysis methods for detecting a marker protein include, but are not limited to, western blotting, ELISA, radioimmunoassay, radioimmunodiffusion, Ouchterlony immunodiffusion, Rocket immunoelectrophoresis, histoimmunostaining, an immunoprecipitation assay, complement fixation assay, FACS and a protein chip. Through the above-listed analysis methods, an amount of antigen-antibody complex formation in a normal control may be compared with an amount of antigen-antibody complex formation in a subject suspected of having a kidney disease, and it can be predicted or confirmed whether a kidney disease actually occurs in a subject suspected of having a kidney disease by determining a significant increase in protein expression level from a marker gene for evaluating renal function.

The term "antigen-antibody complex" used herein refers to a complex of a marker protein for evaluating renal function and an antibody specific thereto, and the amount of antigen-antibody complex formation can be quantitatively measured through a signal size of a detection label.

Measurement of a protein expression level preferably uses ELISA. ELISA includes various ELISA methods such as direct ELISA using a labeled antibody recognizing an antigen attached to a solid support, indirect ELISA using a labeled antibody recognizing a captured antibody in a complex of an antibody recognizing an antigen attached to a solid support, direct sandwich ELISA using another labeled antibody recognizing an antigen in a complex of a solid support-attached antibody and an antigen, and indirect sandwich ELISA using a labeled secondary antibody recognizing an antibody recognizing an antigen after reacting with an antibody-antigen complex attached to a solid support. More preferably, a protein expression level may be measured by a sandwich ELISA method in which an antibody is attached to a solid support to react with a sample, and then the sample is enzymatically colored by attaching a labeled antibody recognizing an antigen of the antigen-antibody complex, or a labeled secondary antibody is attached to an antigen of an antigen-antibody complex to enzymatically develop a color. It can be confirmed whether renal dysfunction occurs by confirming the degree of complex formation between a marker protein for evaluating renal function and an antibody.

In addition, preferably, western blotting is performed using one or more antibodies against the marker for evaluating renal function. For example, total proteins are isolated from a sample, subjected to electrophoresis to isolate the proteins by size, and transferred to a nitrocellulose membrane to react with antibodies. Renal dysfunction can be detected by confirming an amount of a protein produced by gene expression using a method of confirming an amount of antigen-antibody complex production using a labeled antibody. The detection is performed by a method of examining an expression level of a marker gene in a control and an expression level of a marker gene in renal dysfunction-occurring cells. The level of mRNA or proteins may be expressed as the absolute (e.g., µg/ml) or relative (e.g., relative intensity of a signal) difference of the marker protein described above.

In addition, preferably, immunohistochemical staining is performed using one or more antibodies against the marker for evaluating renal function. For example, samples of normal kidney tissue or cells, and cells or tissue of a subject suspected of having renal dysfunction are obtained and fixed, and then paraffin-embedded blocks are prepared by a method widely known in the art. Each block is made into a section with a thickness of several micrometers, attached to a slide glass, and then reacts with one selected from the antibodies by a known method. Afterward, an unreacted antibody may be washed and labeled with one of the above-mentioned detection labels to determine labeling of an antibody under a microscope.

In addition, preferably, a protein chip in which one or more antibodies against the marker for evaluating renal function are arranged at predetermined positions on a substrate and fixed at high density is used. For example, according to a method of analyzing a sample using a protein chip, a protein is isolated from a sample, hybridized with the protein chip to form an antigen-antibody complex, and detected, thereby confirming the presence or expression degree of the protein, and the occurrence of renal dysfunction.

As an analysis method for detecting mRNA of a marker, reverse transcriptase-polymerase chain reaction, competitive reverse transcriptase-polymerase chain reaction, real-time reverse transcriptase-polymerase chain reaction, RNase protection assay, northern blotting, or DNA chip assay may be used, but the present invention is not limited thereto. Through the detection methods, an mRNA expression level in a normal control may be compared with an mRNA expression level in a subject suspected of having a kidney disease, and a significant increase/decrease in mRNA expression level in a renal function evaluation marker gene may be determined, thereby evaluating whether a kidney disease actually occurs in a subject suspected of having a kidney disease.

The measurement of an mRNA expression level preferably uses a reverse transcriptase-polymerase chain reaction or DNA chip using primers specific to a gene used as a marker for evaluating renal function. After the reverse transcriptase-polymerase chain reaction, electrophoresis may be performed to check a band pattern and a band thickness, thereby confirming mRNA expression and its degree of a gene used as a marker for evaluating renal function, and by comparing the result with that of a control, the occurrence of a kidney disease may be simply confirmed or predicted.

Meanwhile, the DNA chip uses a DNA chip in which a nucleic acid corresponding to the marker gene for evaluating renal function or a fragment thereof is attached to a substrate such as glass at high density, and mRNA is isolated from a sample, a cDNA probe labeled with a fluorescent material at its end or inside is prepared and hybridized to the DNA chip, and then the occurrence of a kidney disease can be determined.

Through the above-described detection method, the occurrence of renal dysfunction in a patient exposed to a renal dysfunction-causing material such as a heavy metal or drug may be accurately and simply confirmed or predicted by analyzing the expression pattern of a biomarker, and based on this, it can be used for the treatment of a kidney disease and development of a new drug.

In the present invention, the kidney disease may be, but is not limited to, nephrotic syndrome, kidney cancer, chronic renal failure, diabetic kidney disease, diabetic renal failure, acute pyelonephritis, acute renal failure, hypertensive renal disease, Reye's syndrome, gout, Sjogren's syndrome, Bechet's disease, lupus, candidiasis, nephrotic hemorrhagic fever, leptospirosis, legionellosis, autosomal dominant polycystic kidney disease or hydronephrosis.

Modes of the Invention

Hereinafter, to help in understanding the present invention, exemplary examples will be suggested. However, the following examples are merely provided to more easily understand the present invention, and not to limit the present invention.

EXAMPLES

Example 1. Experimental Animals and Methods

Experiments were carried out using male SD rats (6-week-old, male Sprague-Dawley rats) purchased from Charles River Laboratories (Orient, Seoul, Korea) in accordance with the guidelines of the Ethical Committee of Experimental Animal Testing and Research at Sungkyunkwan University.

1-1. Preparation of Diabetic Animal Models

In one example of the present invention, as diabetic animal models, STZ-administered diabetic animal models and diabetic models using Zucker Diabetic Fatty (ZDF) rats were prepared.

First, as a STZ-administered diabetic animal model, a single dose of STZ (50 mg/kg) was intraperitoneally (I.P.) administered to a Sprague-Dawley rat (white), a blood glucose level was measured daily to evaluate whether the blood glucose level is sufficiently increased, thereby confirming the occurrence of diabetes (approximately 5-fold increase), and here, some experimental groups were treated with an anti-diabetic drug for 4 weeks, and urine was obtained every week to measure an SBP1 level.

Next, as a diabetic model using a Zucker Diabetic Fatty (ZDF) rat, a ZDF rat is a transgenic animal in which diabetes is gradually induced as it grows from birth, and widely used as a human type II diabetic model. Particularly, it has been known that a ZDF rat has diabetes at 8 months after birth and thus is gradually increased in blood glucose level, and when fed a high fat diet, diabetes is rapidly developed. In the present invention, diabetes was induced by providing a high fat diet to the ZDF rat.

1-2. Preparation of Heavy Metal-Induced Chronic Renal Failure Animal Model

Heavy metal (mercury)-induced renal failure animal models were prepared through oral administration of a heavy metal at a very low dose (0.1 mg/kg), a low dose (1 mg/kg) and a medium dose (5 mg/kg) for 30 days and subjected to daily measurement of a urine volume, and the content of proteins contained in the urine obtained for 24 hours after the last administration of the test material was measured. In addition, after collecting blood, the rats of the experimental group and the control were subjected to autopsy to quantify protein levels contained in serum and kidney tissue.

1-3. Preparation of Drug-Induced Renal Failure Animal Model

Drug-induced renal failure animal models were divided into 6 rats for a control and 6 rats for an experimental group by day, cisplatin (CDDP; concentration: 10 mg/kg, solvent: physiological saline, i. p.) known as a drug causing renal dysfunction was injected into the rats. On Day 1, Day 3 and Day 5 after the injection, protein contents in urine obtained for 24 hours were measured in rats of the cisplatin-administered experimental group and the untreated control. In addition, after collection of the urine, the rats of the experimental group and the control were subjected to autopsy, and protein levels in serum and kidney tissue were quantified.

1-4. Electrophoresis (SDS-PAGE)

Proteins were extracted from urine or tissue using a buffer and quantified, thereby preparing a sample. Each sample was mixed with an SDS sample buffer to which a protease or phosphatase inhibitor was added, heated at 95° C. for 5 minutes, and then subjected to electrophoresis.

1-5. Western Blotting

The extracted proteins were dissolved, and transferred to a nitrocellulose membrane. Here, methanol was added to a transfer buffer, and the reaction was performed at 80 V for 1 hour. After the proteins were transferred, the membrane was stained with Ponceau S (within 10 seconds to 1 minute, slightly stained to see a band), and sufficiently washed with DW or PBS for blocking. Here, a blocking buffer was used by dissolving 3 to 5% bovine serum albumin (BSA) in a solution in which TWEEN™ 20 was contained in Tris-buffered saline (TBS). A primary antibody was reacted at 4° C. overnight, rinsed with a wash buffer (surfactant-containing TBS or PBS) to remove unbinding primary antibodies, and then secondary antibodies were reacted. After the secondary antibodies were reacted, unbinding secondary antibodies were rinsed with a washing buffer, and a band was identified using luminol.

1-6. Histological Findings for Kidney and Liver (H&E Staining)

Tissue was rapidly extracted from each of the kidneys and the liver before autolysis, and then blood in the tissue periphery was removed with PBS or normal saline. In the case of the kidney, the outer skin was removed, and the right kidney was divided into two halves and contained in a fixing solution (10% neutral buffered formalin), and in the case of the liver, a part of the largest lobe was cut, and immediately stored in a fixing solution. Afterward, the fixing solution was added at a volume approximately 10 to 20 times the tissue volume to fix the part of the liver for approximately 3 days, and dehydrated using ethanol (70%→90%→95%→100%). After the removal of the alcohol, each slide was paraffinated to a thickness of 5 μm, and stained with Mayer's hematoxylin and eosin (H&E; manufactured by DAKO). Afterward, each slide was deparaffinated using xylene, xylene and moisture in tissue were removed using ethanol (100%→100%→95%→70%). Following washing of a remaining alcohol with tap water, the slide was stained with hematoxylin at room temperature for 30 seconds, remaining hematoxylin was washed, the slide was washed with eosin for approximately 1 minute, and remaining eosin was washed. The moisture in the tissue was removed using ethanol (70%→95%→100%), the ethanol was removed using xylene, the xylene was evaporated, the mounting solution was sprayed, and the resulting slide was cover-slipped and dried at room temperature.

1-7. Immunostaining of SBP1 in Kidney Tissue

After each slide prepared in Example 1-6 was treated with xylene to remove paraffin, the xylene and moisture in tissue were removed using ethanol (100%→100%→95%→70%), the slide was washed with tap water, heated in a microwave oven for 20 minutes for antigen retrieval of the peeled tissue on the slide using a sodium citrate buffer, cooled with tap water, immersed in PBS for 5 minutes at room temperature, and then treated with an endogenous peroxidase (methanol:hydrogen peroxide=3:1) to remove unnecessary antigens of the tissue (3 to 5 minutes at room temperature). After the reaction, the slide was washed with PBS twice for 5 minutes, the tissue was blocked with a blocking solution prepared with normal goat serum, SBP1 antibodies were diluted in the blocking solution and plated on the slide to allow a reaction at 4° C. overnight. After the reaction, the slide was washed with a washing solution three times for 5 minutes, and secondary antibodies were attached (30 minutes to 1 hour at room temperature). After the reaction, the slide was washed with a washing solution three times for 5 minutes, reacted with avidin-biotinylated HRP for 30 minutes, and washed with a washing solution three times for 5 minutes. Afterward, the washed slide was allowed to react with a DAKO DAB solution for approximately 1 minute, the remaining solution was removed, the slide was stained with a hematoxylin solution for approximately 30 seconds to 1 minute at room temperature, and then the remaining solution was removed. The slide was treated with a blueing solution (ammonium hydroxide 0.5%) for approximately 30 seconds, the remaining solution was removed, and moisture in tissue was removed using ethanol (ethanol 70%→95%→100%). Subsequently, the ethanol in the tissue was removed with xylene, after the elimination of xylene, the slide was treated with a mounting solution, coverslipped and then dehydrated at room temperature.

Example 2. Verification of Diabetic and Renal Failure Animal Models 2-1. Verification of Model with Diabetes Induced by STZ Administration To verify a diabetic animal model induced by STZ administration according to Example 1-1 of the present invention, an experiment was carried out by designing the experimental model as described in FIG. 1A.

Figure 1B:
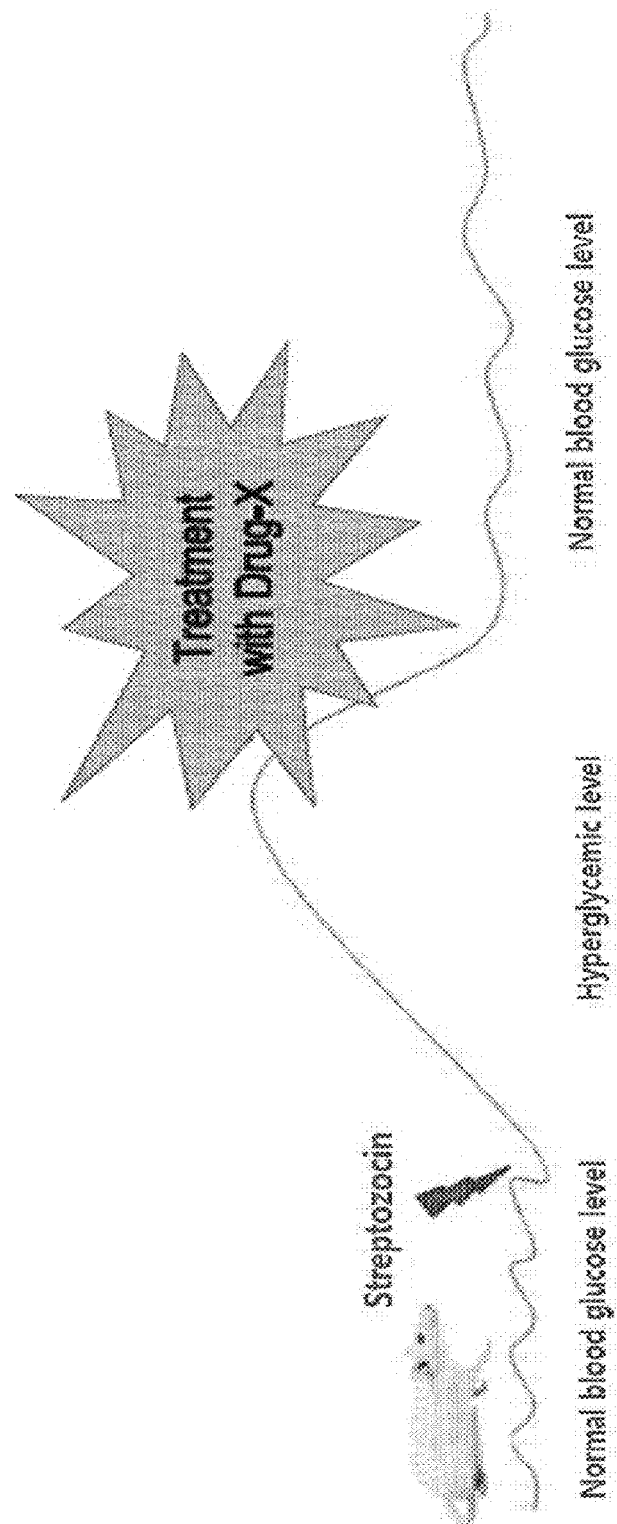
Figure 1C:
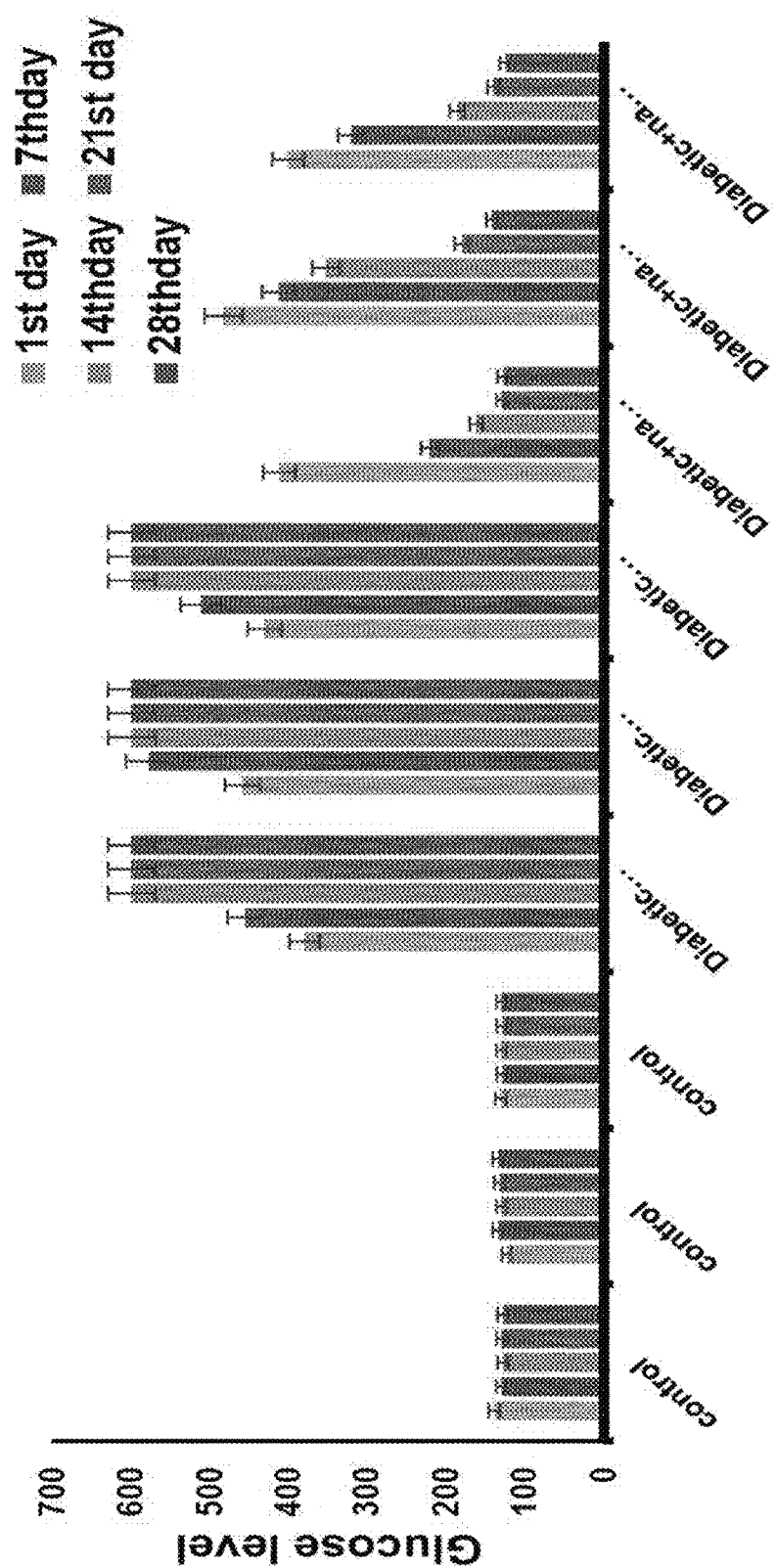
FIG. 1C shows a result of measuring a blood glucose concentration by administering an anti-diabetic drug to a diabetic animal and FIG. 1D shows a result of measuring microalbumin in urine, which is one of the most important factors of a diabetic kidney disease, and as shown in FIGS. 1C and 1D, it was confirmed that, after STZ is administered to a rat, a microalbumin concentration in urine, which is one of the representative indicators for renal dysfunction caused by diabetes, increases, and the experimental animal model is well presented to predict diabetic renal failure.
Figure 1D:
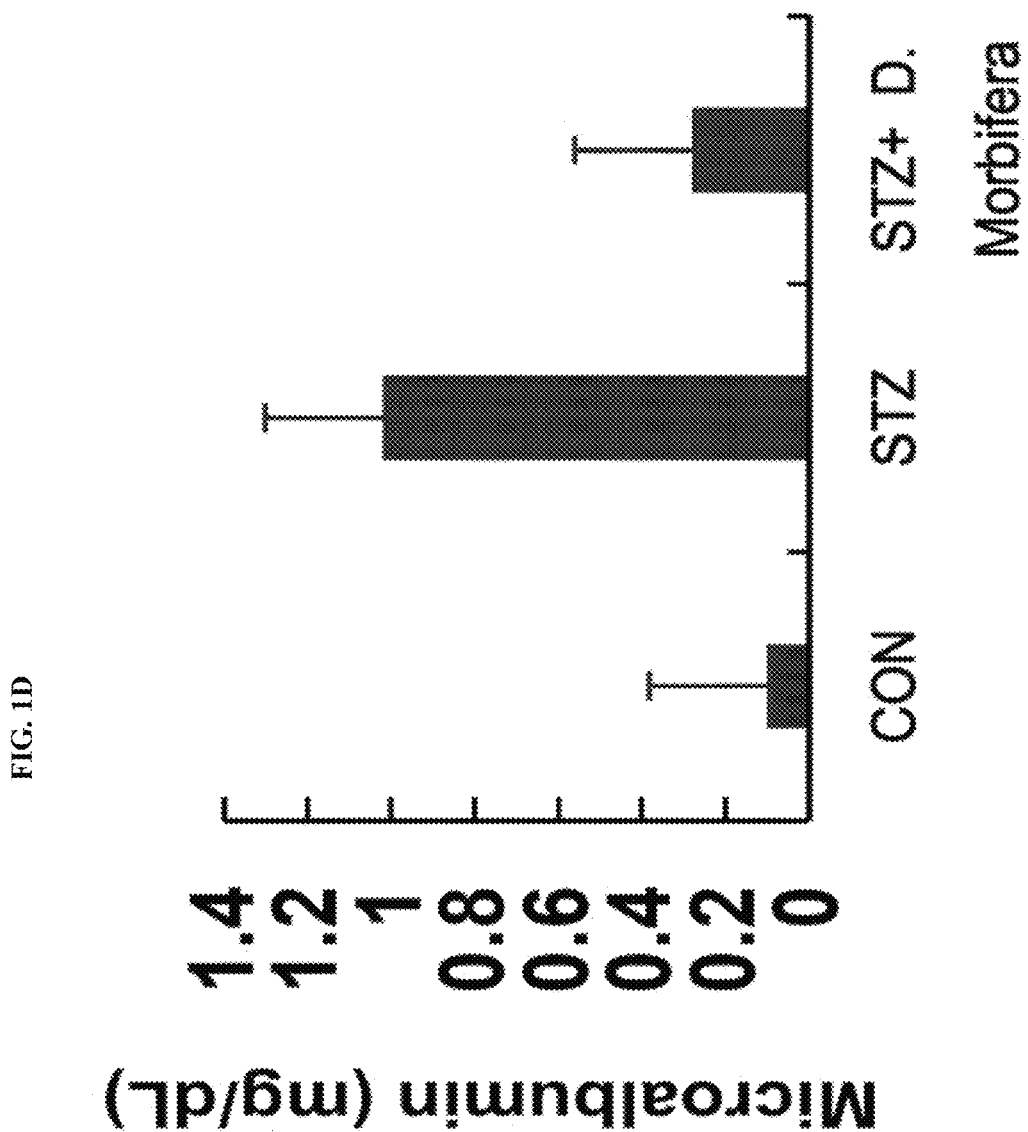

As a result, as shown in FIGS. 1B and 1C, in the control, a normal blood glucose level was shown, but in the STZ-administered animal group, a blood glucose level was increased approximately 6-fold or higher (600 mg/dL or more) compared to the control. However, in an experimental group in which diabetic animals are treated with an antidiabetic drug, it was confirmed that a blood glucose level was decreased gradually on Day 7, Day 14 and Day 21, and decreased to almost the normal level on the last day, Day 28. In addition, as a result of measuring microalbumin in urine, which is one of the most important factors of a diabetic kidney disease, it can be confirmed that, as shown in FIG. 1D, in the STZ-administered group, the microalbumin in urine was significantly increased approximately 10-fold or more compared to the control, and in the anti-diabetic drug-administered experimental group, the microalbumin in urine was decreased to the control level.

Figure 2A:
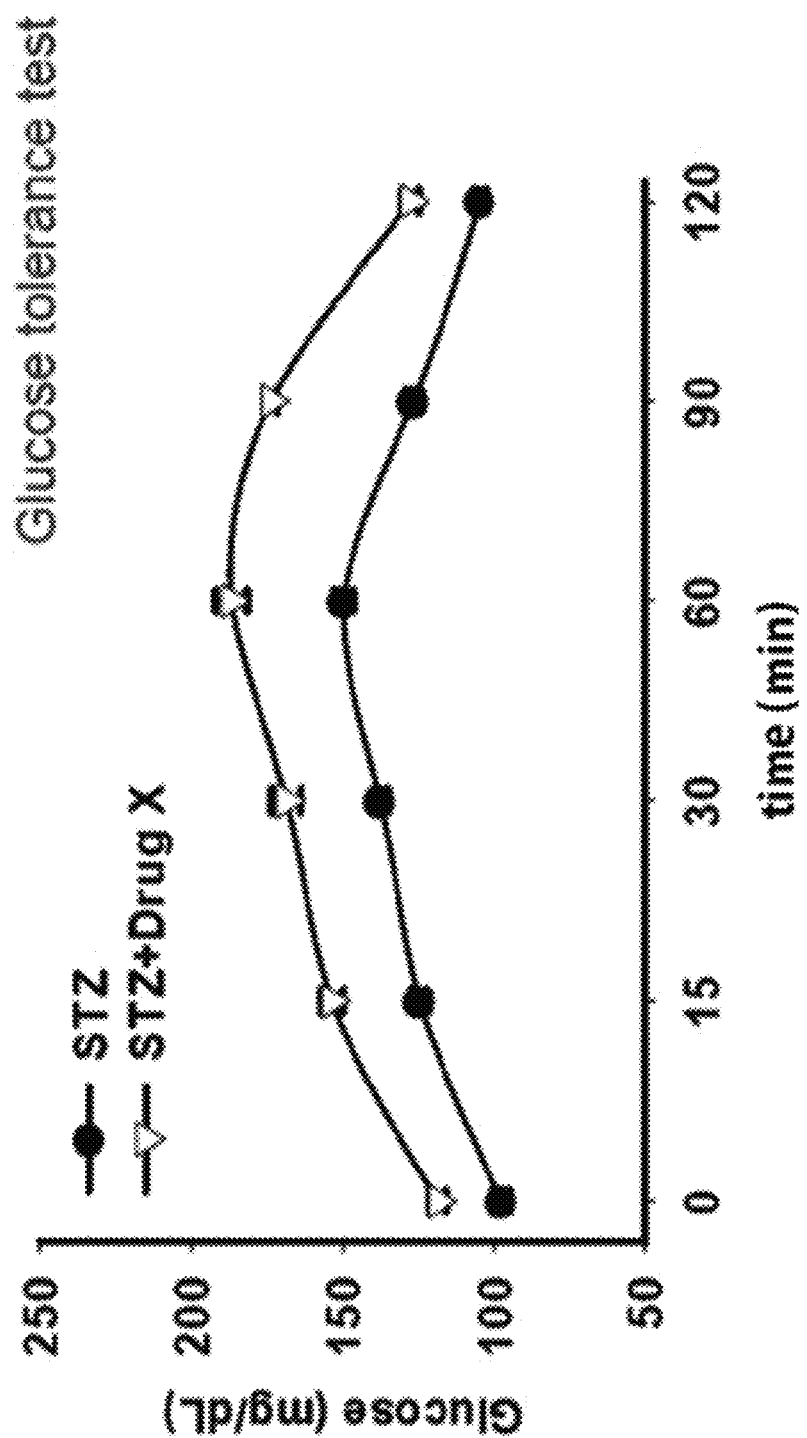
FIGS. 2A and 2B illustrates important experimental methods of examining effects of an anti-diabetic drug.
Figure 2B:
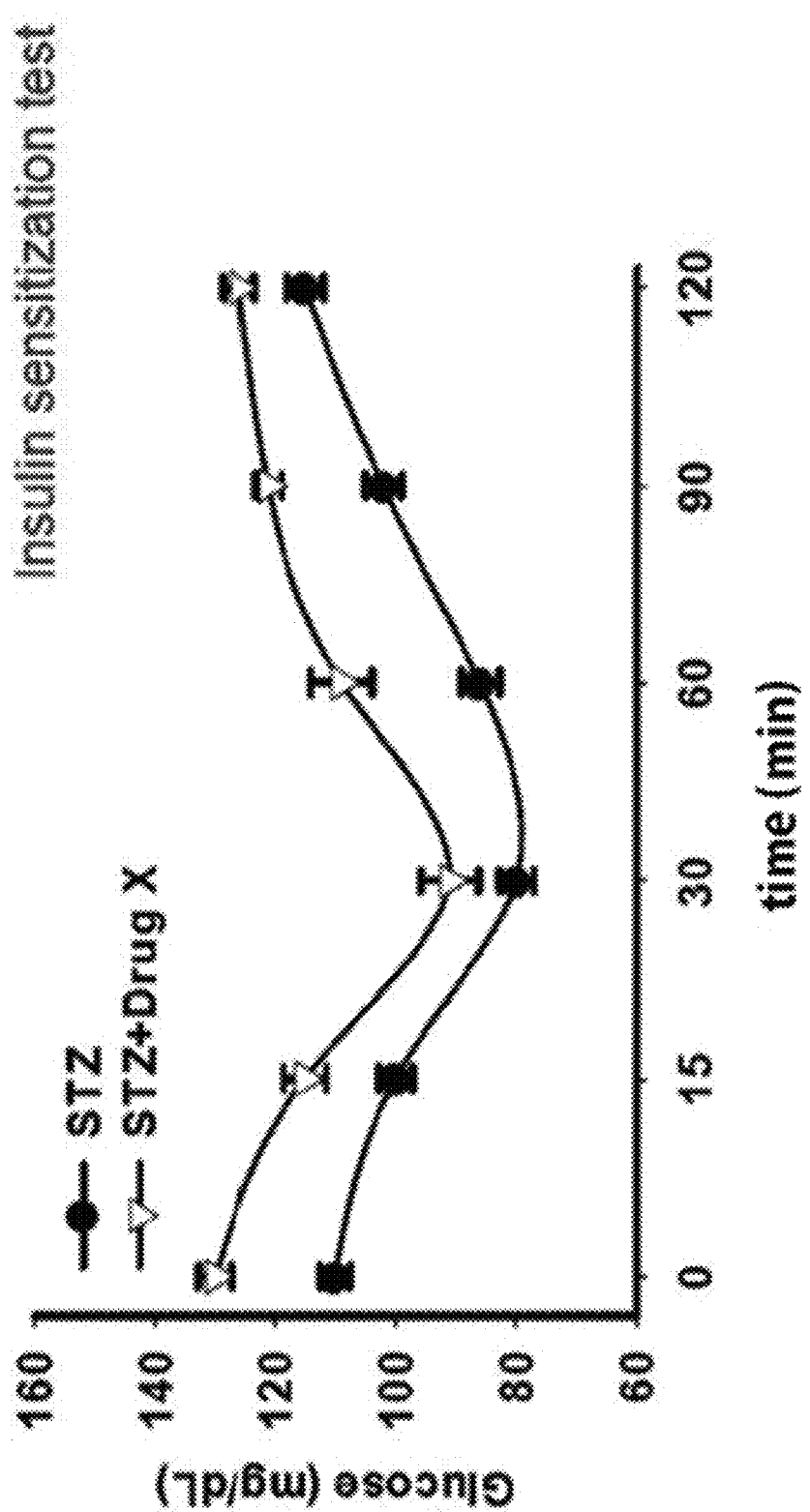

In addition, to confirm the effect of an anti-diabetic drug, a glucose tolerance test and an insulin sensitization test were performed. As a result, as shown in FIGS. 2A and 2B, it can be confirmed that all of the anti-diabetic drug-administered experimental group, compared with the diabetes-induced experimental group, respond sensitively to glucose in blood.

Figure 3A:
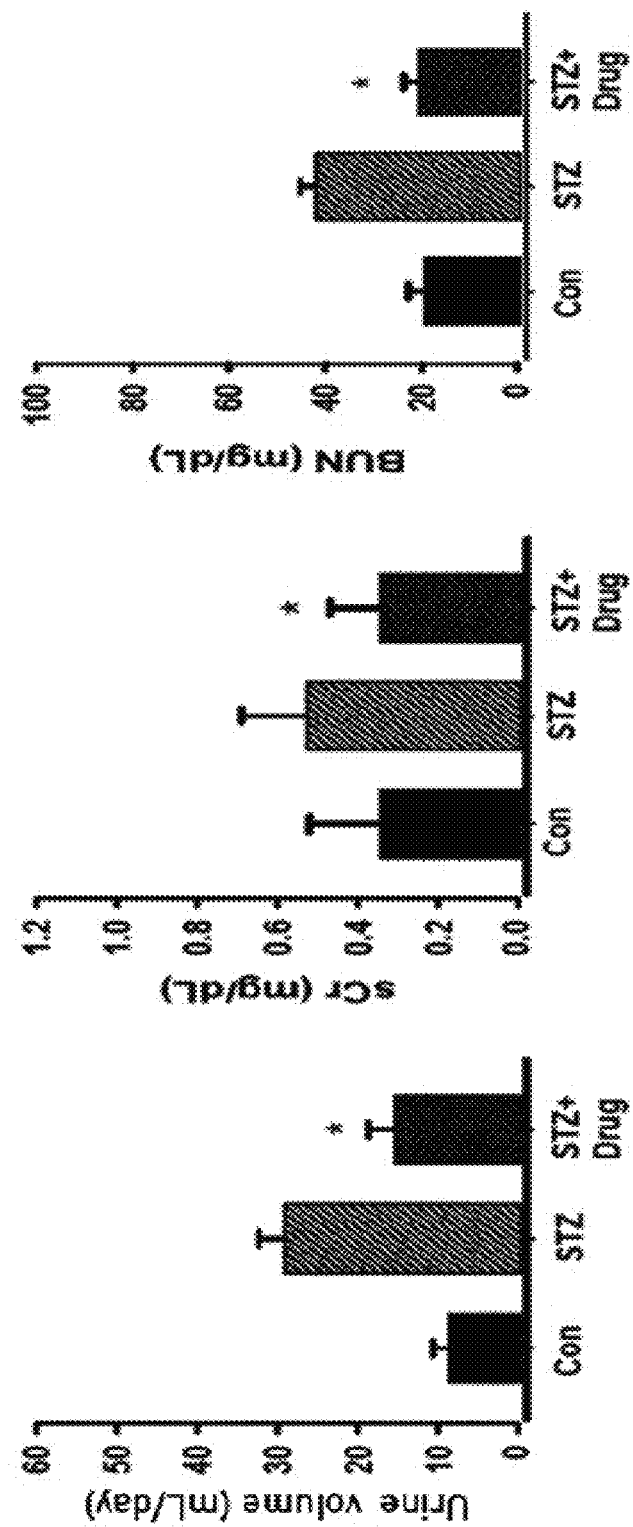
FIG. 3A shows a result of measuring a urine volume, BUN and creatinine levels to confirm whether renal failure occurs in a STZ-administered diabetic animal model.

Then, it was confirmed whether renal failure occurs in a diabetic animal model induced by STZ administration. As a result, as shown in FIG. 3A, in the diabetic animal, a urine volume (ml) was increased 3-fold or higher compared to the control (one of the representative clinical symptoms of diabetes), and a decrease in urine volume by the administration of an anti-diabetic drug was shown, and it was confirmed that, in the STZ-administered group, BUN and creatinine, which are the major index factors of nephrotoxicity, were increased approximately 2-fold or higher, compared to the control. It can be seen that, in the anti-diabetic drug-administered group, the BUN and creatinine levels are decreased to a normal range.

From the above results, it can be confirmed that renal failure was induced in the diabetic animal models, whereas BUN and creatinine were decreased and thus renal failure was protected in the anti-diabetic drug-administered group.

In addition, to confirm the degree of histological damage to the kidney in the diabetic animal model, kidney tissue was fixed in 10% neutral formalin, paraffinated and then sliced to a thickness of 5 μm. After then, the sliced tissue was deparaffinated and stained with hematoxylin & eosin (H&E).

Figure 3B:
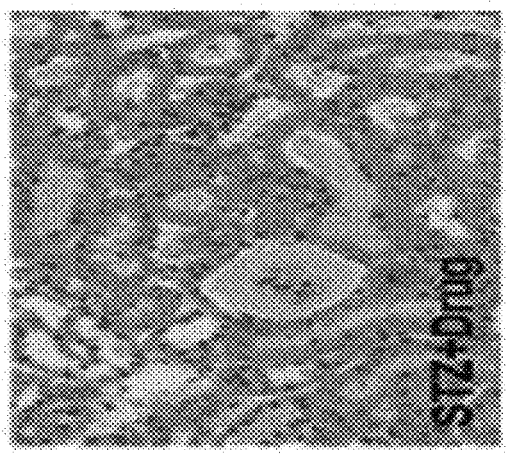
FIG. 3B shows a result of identifying a degree of histological damage to the kidney in a STZ-induced diabetic animal model by hematoxylin & eosin (H&E) staining.
Figure 3B:
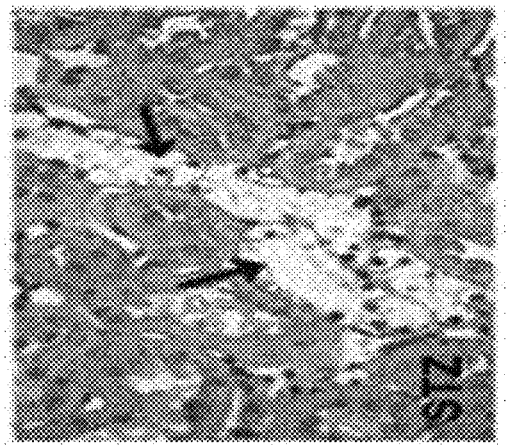
Figure 3B:
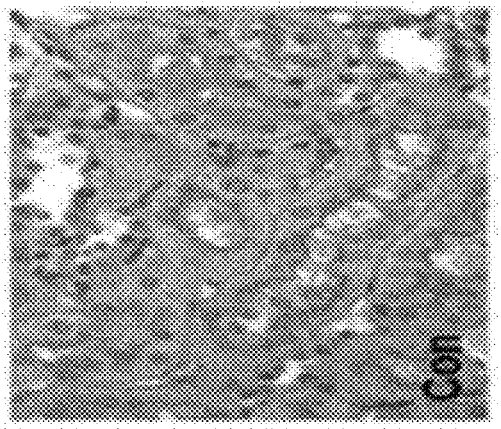

As a result, as shown in FIG. 3B, it was confirmed that glomerular and tubular damage is clearly shown in the diabetic animal model, and histological findings similar to those of the normal group (control) were shown in the anti-diabetic drug-administered experimental group.

Figure 3C:
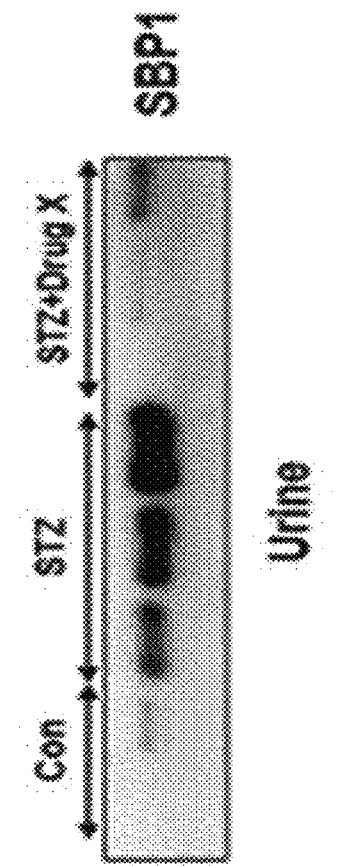
FIG. 3C shows a result of confirming whether SBP1 in urine is increased in a diabetic renal failure animal model, thereby showing significant increases in SBP1 and NGAL in a diabetic animal and proving that SBP1 in urine is very sensitively increased by diabetic kidney failure.
Figure 3C:
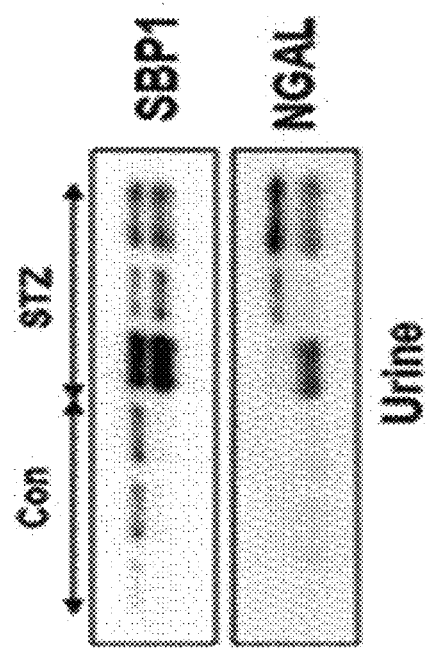

According to the results, it can be estimated that when diabetes is induced, chronic renal failure occurs. In addition, as shown in FIG. 3C, SBP1 was detected at a high level in the urine of a diabetic experimental animal, and SBP1 detection was significantly decreased by the administration of an anti-diabetic drug. Therefore, the result demonstrated that SBP1 can be an indicator for early diagnosis of renal failure caused by diabetes.

2-2. Verification of Zucker Diabetic Fatty (ZDF) Diabetic Model

Figure 4A:
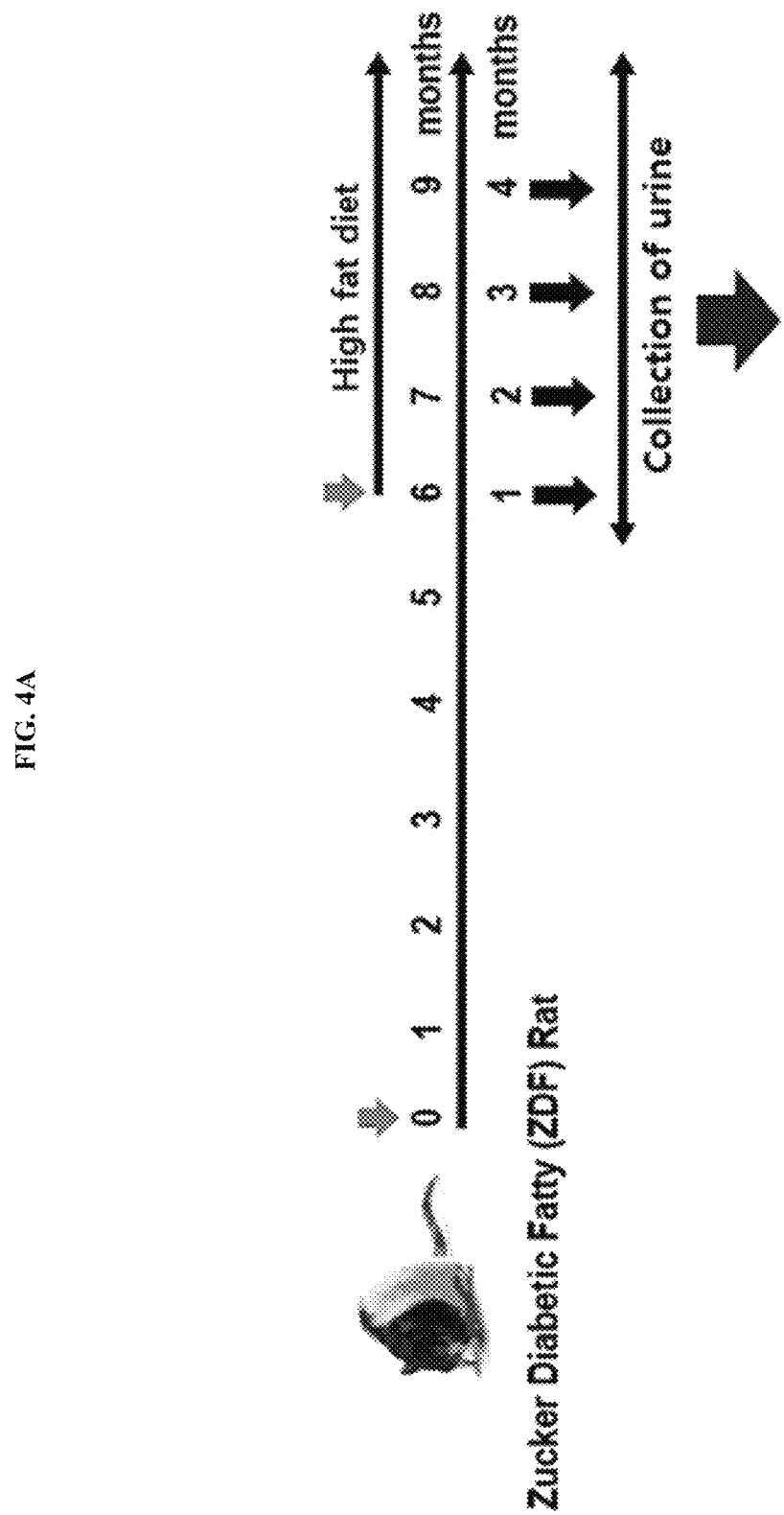
FIG. 4A shows the design of manufacturing diabetic models using a Zucker Diabetic Fatty (ZDF) rat well known as a type II diabetic animal model.

As show in FIG. 4A, experiments were carried out with ZDF rats, which are Zucker Diabetic Fatty (ZDF) diabetic models prepared according to Example 1-1 of the present invention, as an experimental model. More specifically, the ZDF rats were fed a high fat diet for 4 months from 6 months after birth, the urine of each rat was obtained every month to evaluate whether SBP1 is detected in the urine.

In addition, after the ZDF rat was fed a high fat diet, a blood glucose level was measured every month to check whether diabetes was induced.

Figure 4B:
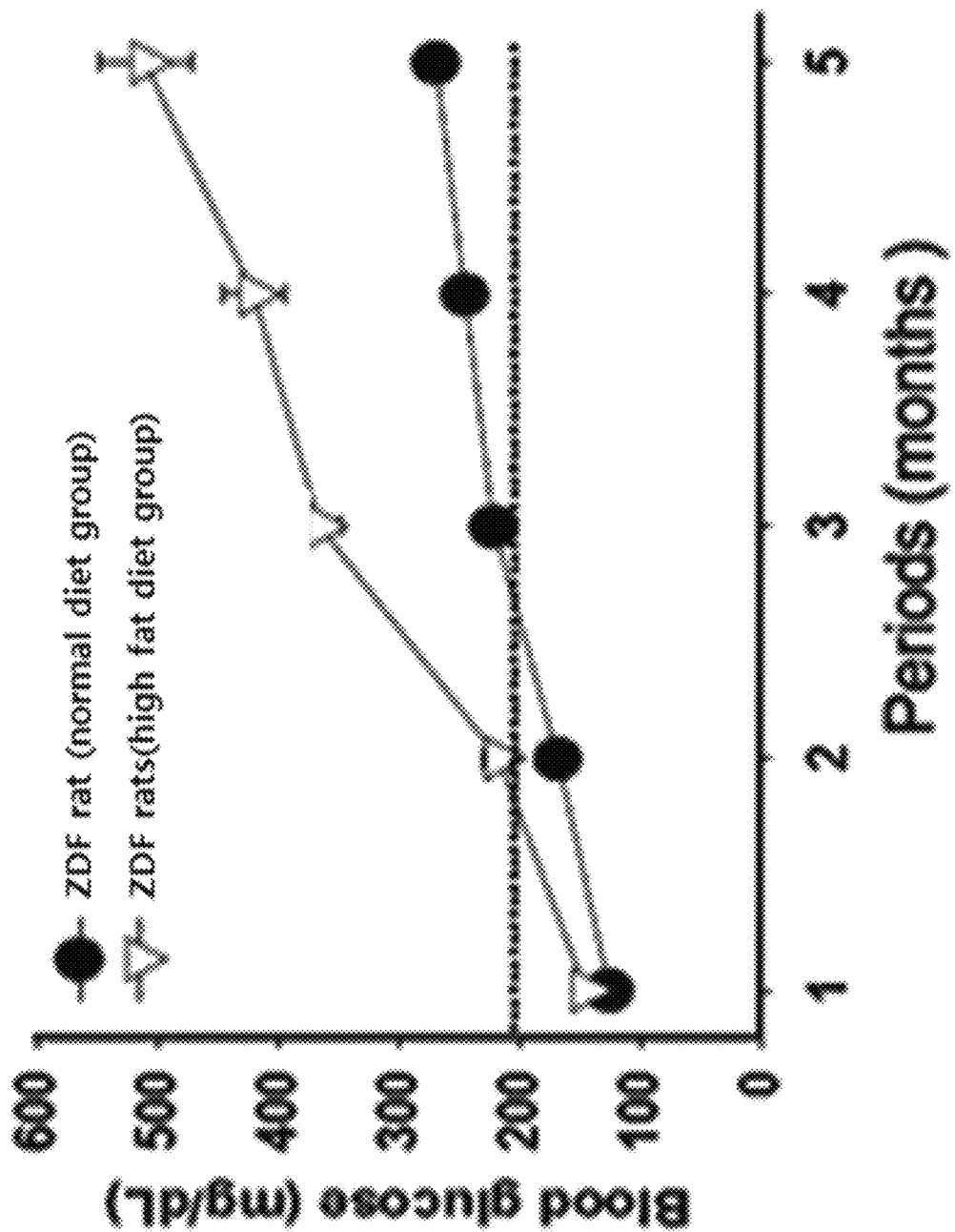
FIG. 4B shows a result of measuring a blood glucose level every month after the ZDF rat is fed a high fat diet.

As a result, as shown in FIG. 4B, it can be confirmed that, in an experimental group fed a high fat diet, a blood glucose concentration was increased to 600 mg/dL or more according to time.

Figure 4C:
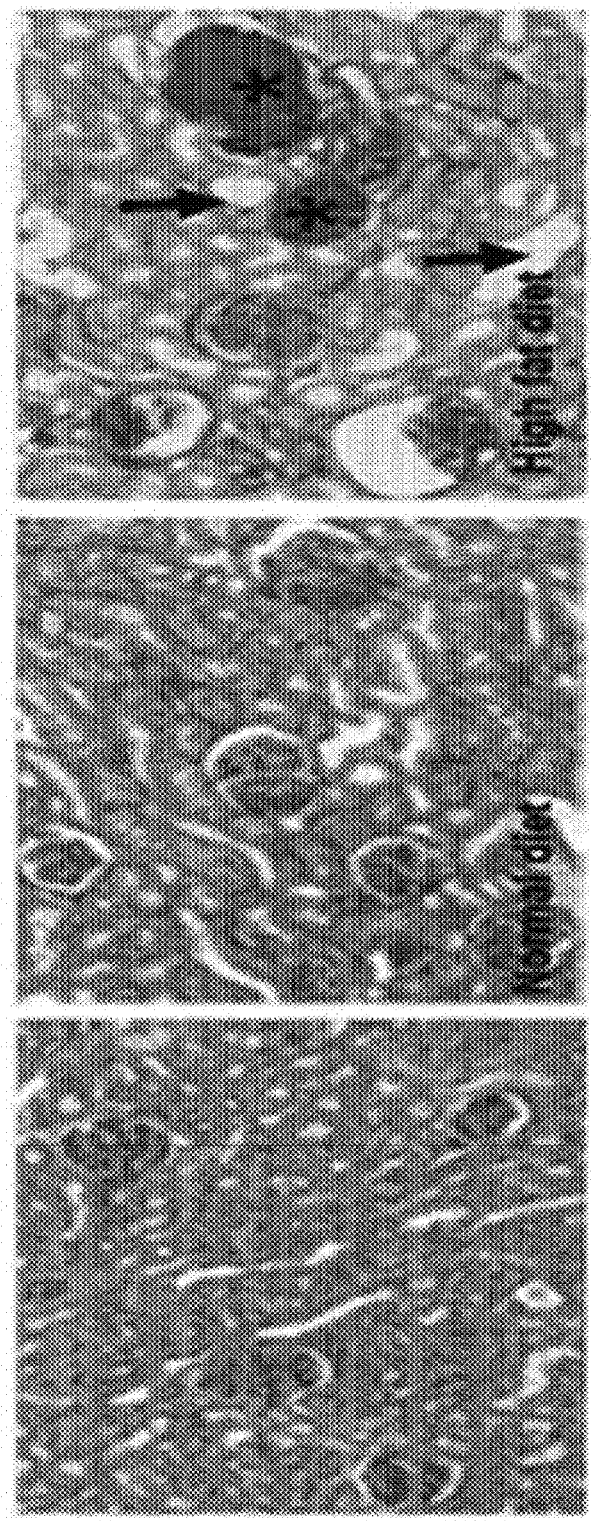
FIG. 4C shows a result of confirming a degree of histological damage of the kidney using H&E staining after the ZDF rat is fed a high fat diet for 5 months and then subjected to autopsy.
Figure 4D:
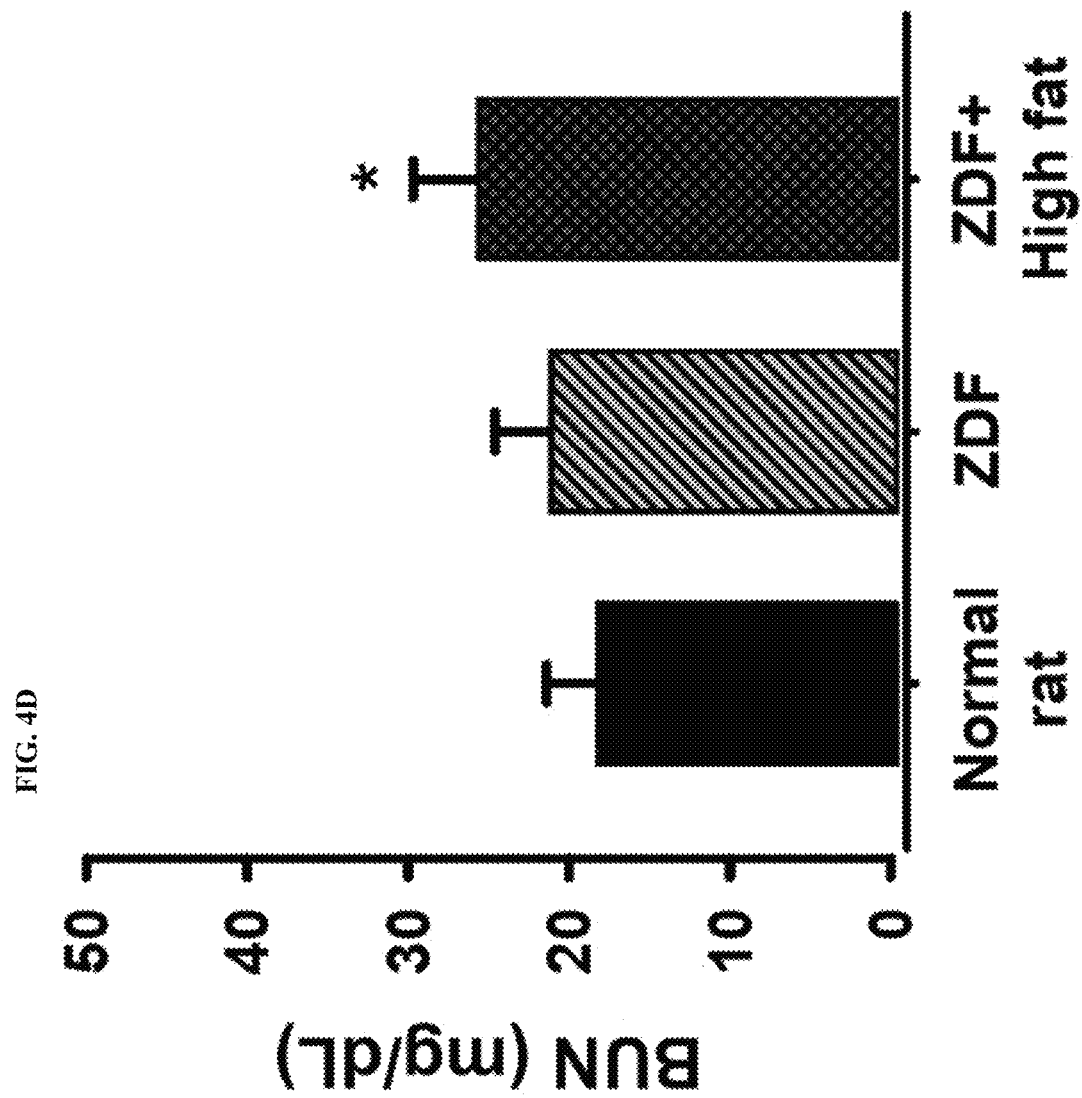
FIG. 4D shows a result of comparing BUN levels according to a high fat diet in the ZDF diet and a normal rat.
Figure 4E:
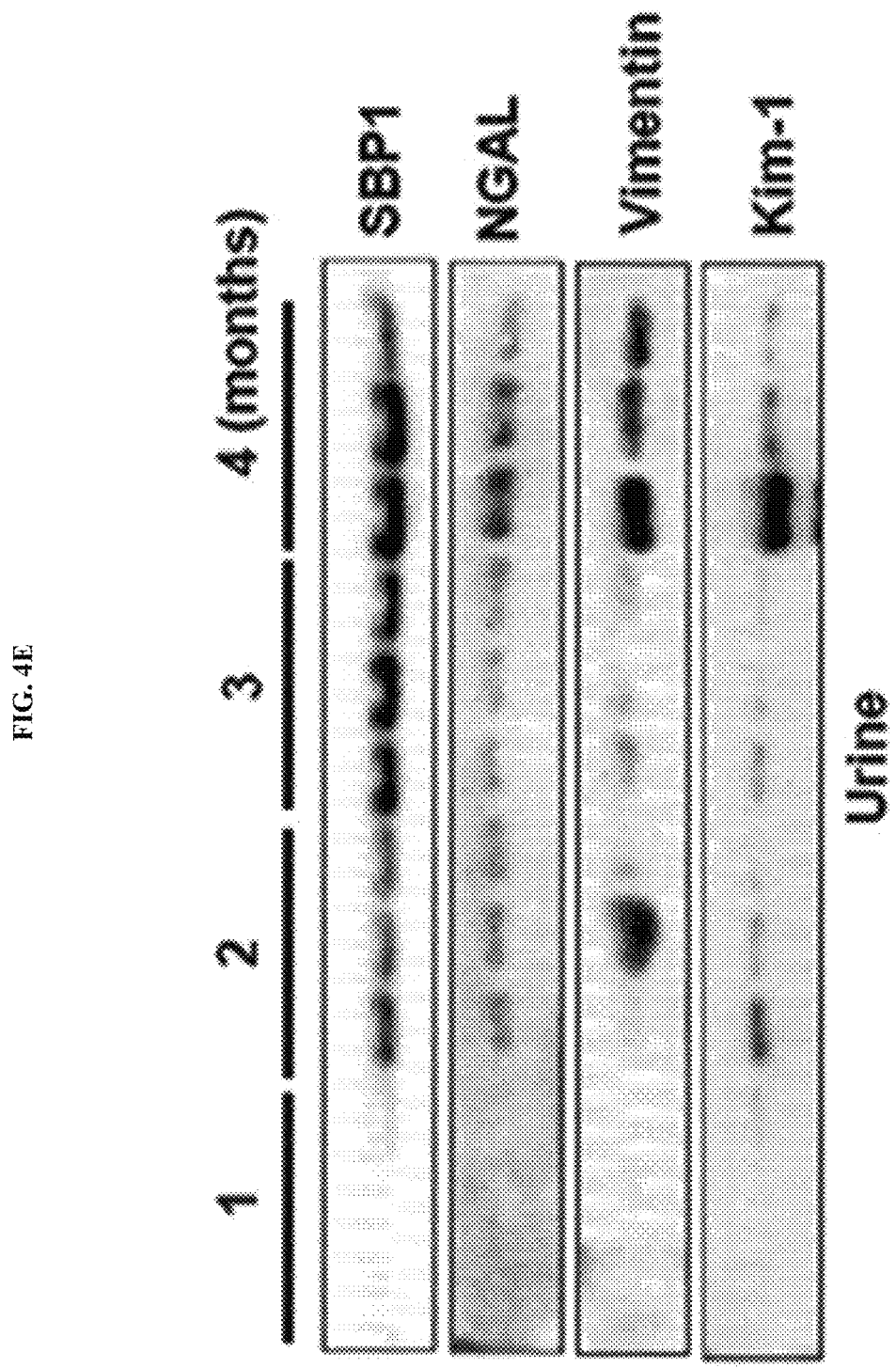
FIG. 4E shows a result of measuring SBP1, NGAL, vimentin and KIM-1 contents in urine after ZDF rats are fed a high fat diet for 4 weeks.

The degree of histological damage in the kidney of the Zucker Diabetic Fatty (ZDF) diabetic model was confirmed through hematoxylin & eosin (H&E) staining. As a result, as shown in FIG. 4C, it can be specifically confirmed that, the glomeruli of the kidney were damaged due to a high fat diet, and cell damage in the renal tubule was severe, and as shown in FIG. 4D, it can be confirmed that, compared with the normal rat, the BUN level in the high fat diet ZDF rat was significantly increased. In addition, as shown in FIG. 4E, when hyperglycemia was induced by a high fat diet, it was confirmed that the SBP1 level in urine was gradually increased in a time-dependent manner. Particularly, SBP1 was increased from two weeks after the high fat diet, compared with NGAL and KIM-1, which are conventional nephrotoxicity indicators, demonstrating that SBP1 is very sensitive in early diagnosis of renal failure.

2-3. Verification Research in Diabetic Patients

From these results, to investigate whether the above results coincide with clinical results, urine samples of diabetic patients were provided from the Korea University Hospital and examined as to whether SBP1 was detected in the urine of a patient through western blotting.

Figure 5:
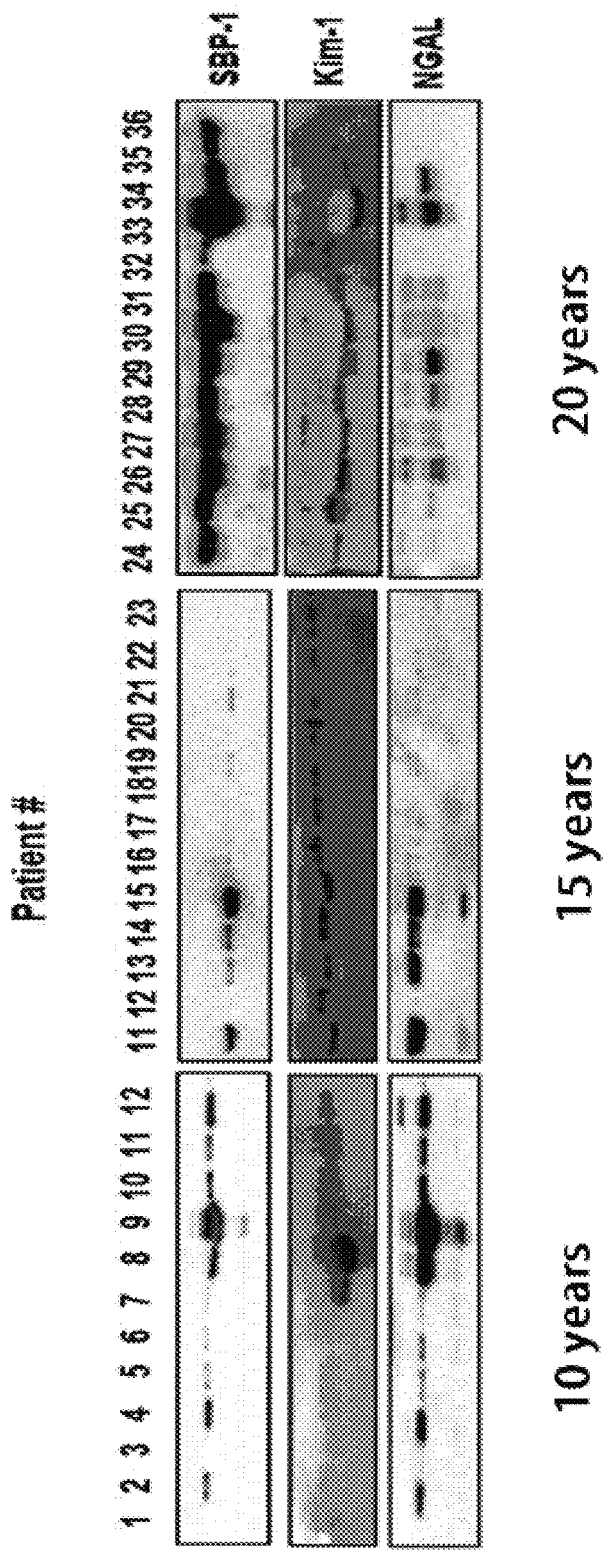
FIG. 5 shows a result of measuring SBP1, Kim-1 and NGAL contents in the urine of diabetic patients.

More specifically, as a result of testing urinary SBP1 for 36 diabetic patients, it can be confirmed that, in most patients, SPB1 was detected, and particularly, urinary SBP1 is increased in a patient as the diabetic duration is extended (see FIG. 5).

Figure 6:
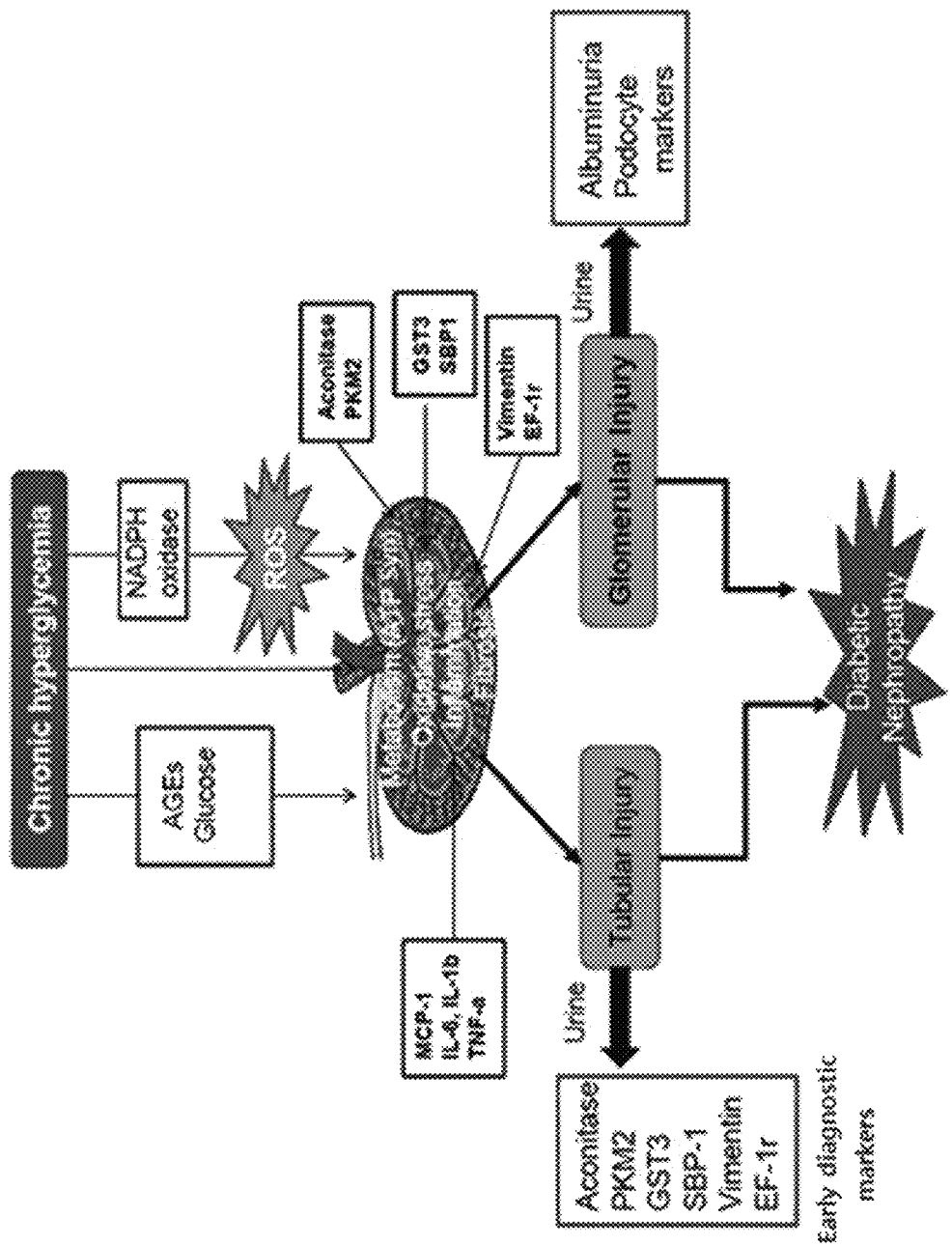
FIG. 6 illustrates how the renal function is deteriorated in a chronic hyperglycemic (diabetic) patient, and shows indicators (i.e., biomarkers) detected according to a progression stage of diabetes.

FIG. 6 illustrates the action mechanism showing whether SBP1 is generally excreted into urine in a type II diabetic patient, showing that oxidative damage in the kidney is increased because of a high fat diet, the kidney is damaged by activation of various types of inflammatory factors, and SBP1 is highly expressed in kidney cells, and therefore, it was first demonstrated that, when proximal tubule cells of the kidney are damaged, the SBP1 was released into the urine.

Based on these results, FIG. 6 illustrates the mechanism in which renal failure is caused in a diabetic patient and the types of biomarkers for diagnosing renal failure by step. It can be shown that, in the early stage of diabetes, SBP1 excretion affects the stage of ATP synthesis using glucose metabolism, as diabetes progresses, oxidative damage to kidney tissue occurs, resulting in cell death by inflammation. Finally, it can be seen that renal function is impaired by inducing renal fibrosis.

Example 3. Problem of Using Conventional Marker for Renal Dysfunction

According to this example of the present invention, it was confirmed whether type II diabetes renal failure animal models have renal failure due to diabetes as clinically shown. As a result, it was demonstrated that all of two types (type I and type II) of diabetic models have renal dysfunction. Therefore, it was proved that BUN, creatinine and microalbumin, which are markers for diagnosing renal function, are highly detected in diabetic rats.

In addition, in the conventional test for diagnosing renal dysfunction, the induction of renal dysfunction by cisplatin/$HgCl_2$ was diagnosed by measuring representative markers, such as serum creatinine (SCr), BUN and glucose contained in urine, LDH, aspartate aminotransferase (AST) and total protein.

3-1. Confirmation of Induction of Chronic Renal Dysfunction by Heavy Metal (Mercury, $HgCl_2$)

Subsequently, following oral administration (1 mg/kg and 5 mg/kg) of representative nephrotoxic materials, that is, a heavy metal (mercury, $HgCl_2$) for a month, pathological findings of kidney tissue were obtained through H&E staining.

Figure 7A:
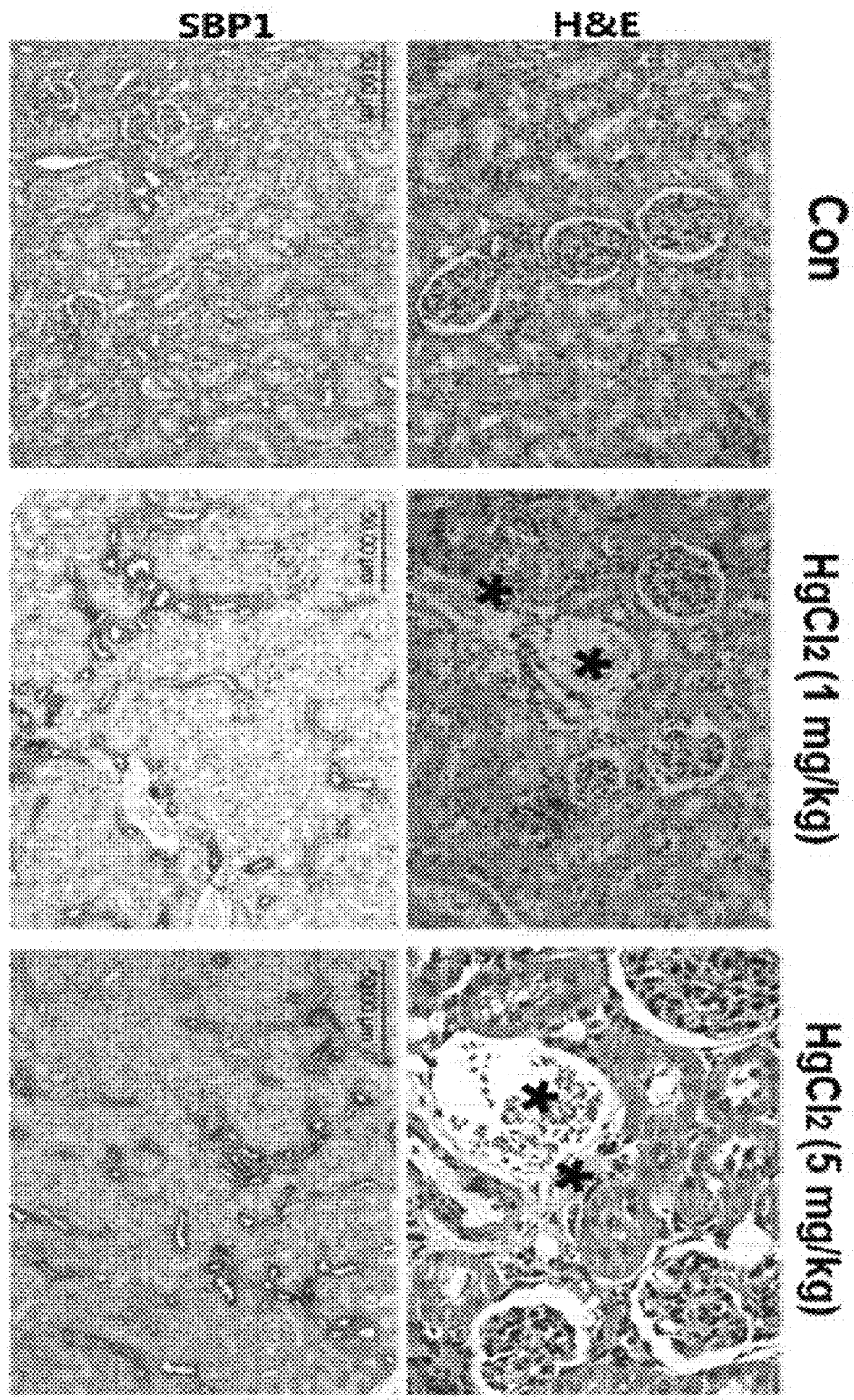
FIG. 7A shows a result obtained by inducing a chronic deterioration of renal function after oral administration of a heavy metal (mercury, $HgCl_2$) as a representative nephrotoxic material (0.1, 1 mg/kg and 5 mg/kg) for 1 month, and pathological findings for kidney tissue are obtained by H&E staining.

As a result, as shown in FIG. 7A, it was confirmed that renal failure was induced by chronic administration of a low dose (0.1 mg/kg) of mercury, and therefore, SBP1 expression in renal tissue was also increased when a low dose of mercury was orally administered.

Figure 7B:
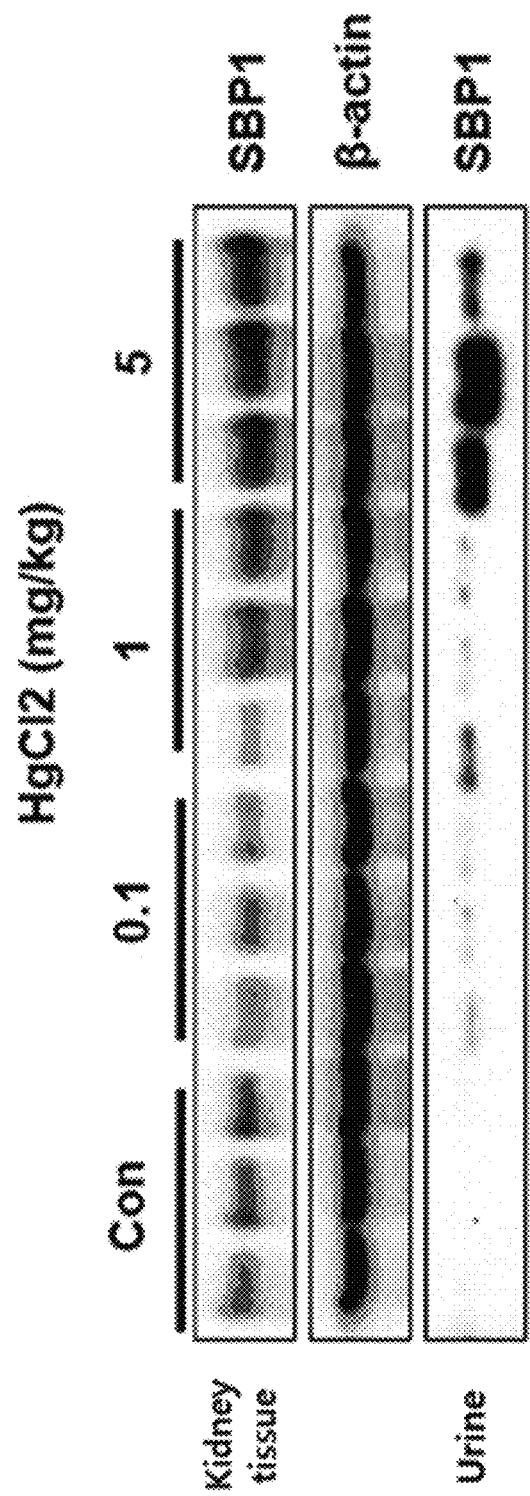
FIG. 7B shows expression of SBP1 in kidney tissue by treatment of a heavy metal (mercury, $HgCl_2$), which is a nephrotoxic material.
Figure 7C:
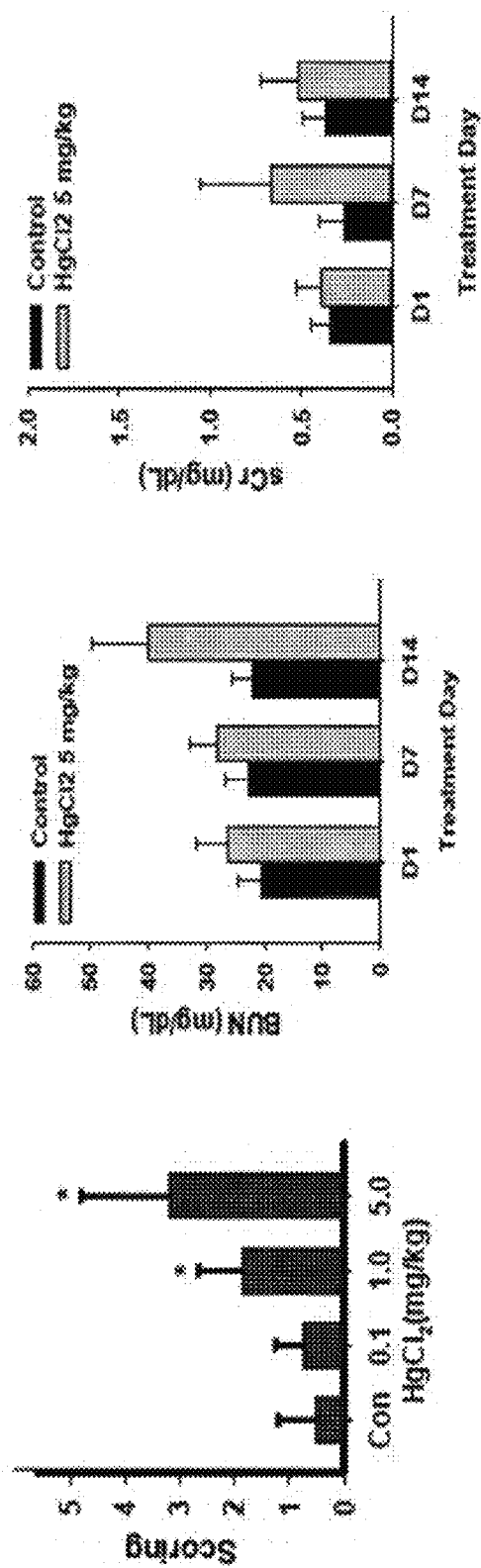
FIG. 7C shows the evaluation indices for histological injury, and blood urea nitrogen (BUN) and creatinine levels after a small amount of $HgCl_2$ (0.1 mg/kg) is administered for a month.

In addition, as shown in FIGS. 7B and 7C, it was confirmed that, when a very small dose (0.1 mg/kg) of mercury was administered for a month, although histological damage, and BUN and creatinine levels were not increased, SBP1 was detected in urine. Accordingly, it was estimated that urinary SBP1 is first detected in urine before renal function is impaired due to chronic exposure to toxic materials such as heavy metals.

3-2. Confirmation of Induction of Renal Dysfunction by Cisplatin (CDDP)

As described in Example 1-2 of the present invention, following administration of a representative nephrotoxic drug (cisplatin; 10 mg/kg, I.P.) to a rat, urine samples were collected using a metabolic cage (cage for metabolite analysis) for 24 hours on Day 1, 3 and 5. A supernatant was obtained by centrifuging each urine sample at 3000 g for 15 minutes, and stored in a freezer at −80° C. Following the urine collection, experimental animals were anesthetized with carbon dioxide to collect blood from the abdominal aorta, and after natural death due to bleeding, the kidneys and liver were extracted. A supernatant was obtained by centrifuging each blood sample at 1500 g for 15 minutes, and stored in a freezer at −80° C. The obtained urine and blood samples were subjected to detection of conventional markers using a test kit corresponding to each parameter.

Figure 8A:
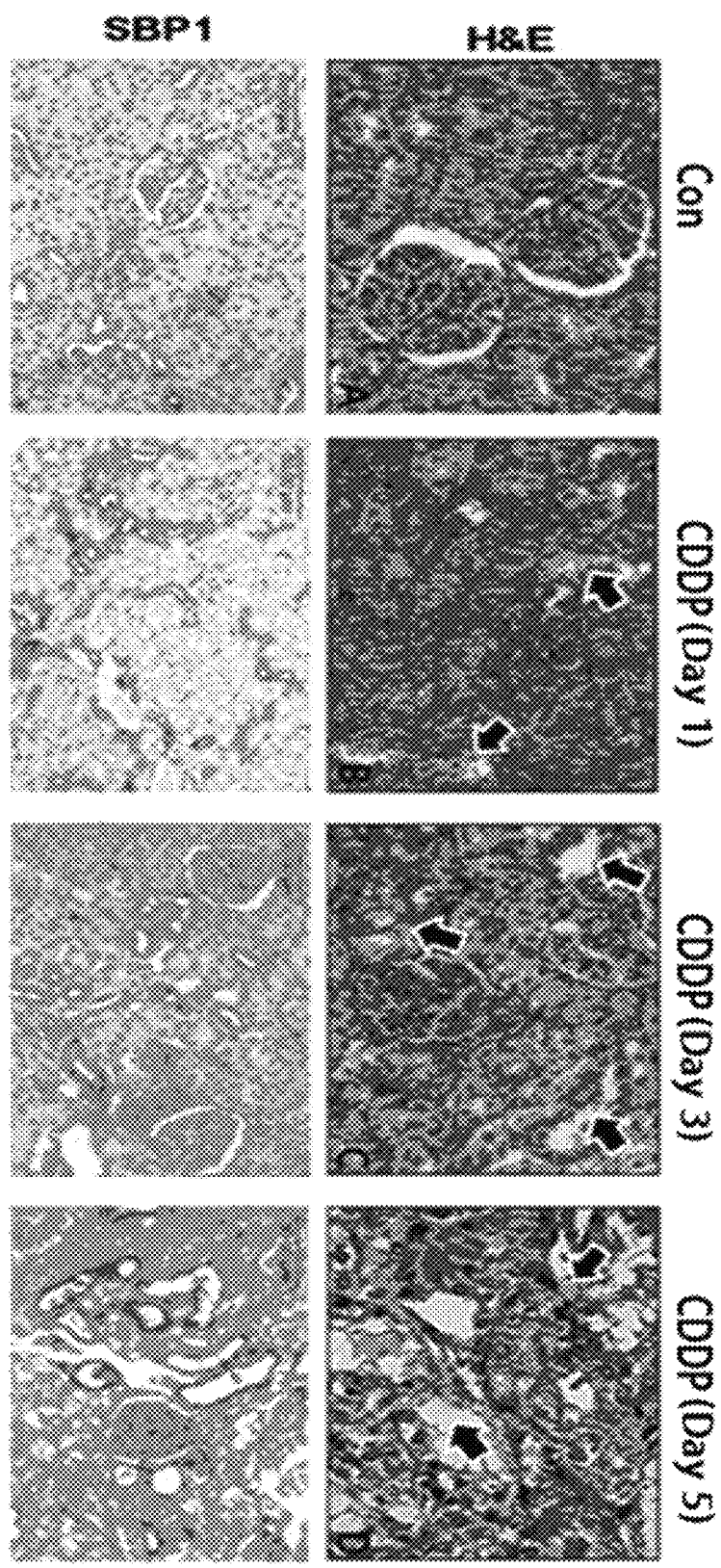
FIG. 8A shows the histological injury of the kidney on Day 1, Day 3 and Day 5 after administration of the anti-cancer agent cisplatin (CDDP), which is a representative nephrotoxic material, proved by histochemical staining for SBP1 expressed in kidney tissue.

As a result, as shown in FIG. 8A, kidney tissue began to be mildly damaged on Day 1 after cisplatin administration, and most tubules were severely damaged on Day 5, and thus it was demonstrated that SBP1 is intensively stained in the damaged part of the kidney tissue.

Figure 8B:
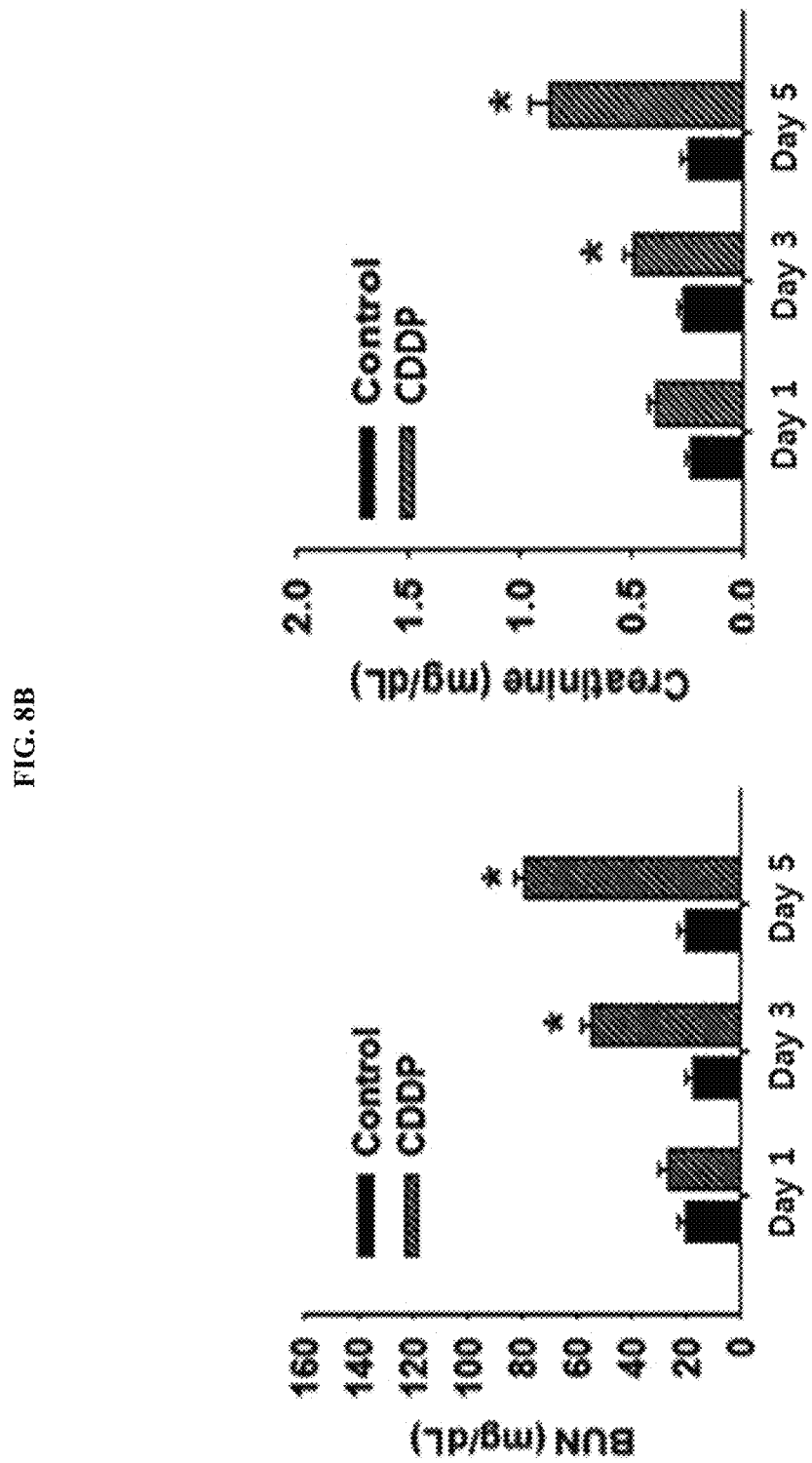
FIG. 8B shows conventional markers for abnormal renal function, such as serum creatinine, BUN, and urinary SBP1 levels, measured for an untreated control and a drug-administered experimental group.

From the result, as shown in FIG. 8B, it can be confirmed that there was no significant differences in nephrotoxicity indicators such as serum creatinine and BUN on Day 1, compared with those of the control, but after CDDP administration, the indicators were significantly increased on Day 3, and increased approximately 3 to 5-fold or more on Day 5, compared with the control.

Figure 8C:
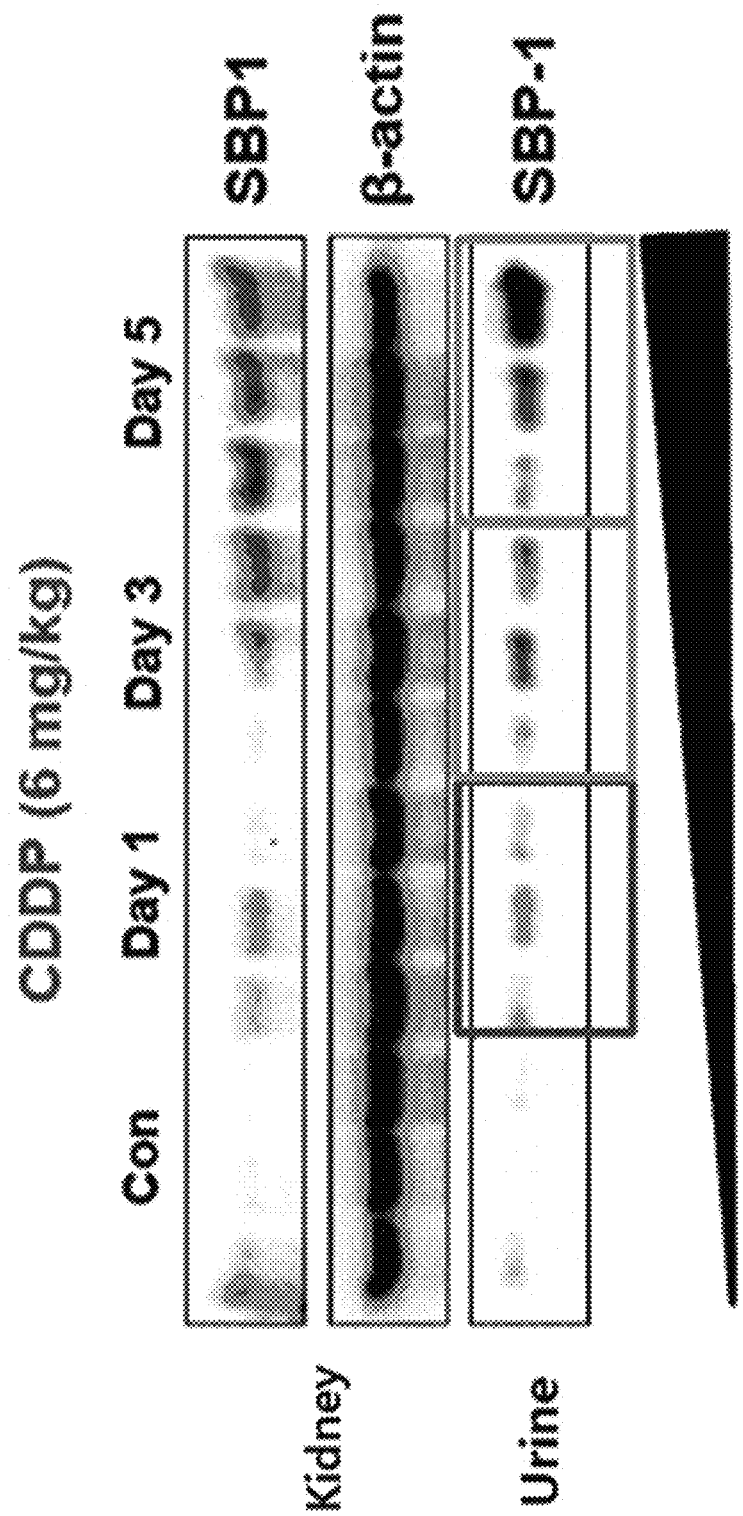
FIG. 8C shows SBP1 levels in the kidney and urine according to CDDP administration, quantified by western blotting.

In addition, as shown in FIG. 8C, it can be confirmed that a urinary SBP1 level, which is a nephrotoxicity indicator, was quantified by western blotting, confirming that the urinary SBP1 level was increased on Day 1 after CDDP administration, and detected at a very high level on Day 5.

Taken the above results together, it can be confirmed that SBP1 is excreted into urine earlier than the conventional nephrotoxicity indicators such as serum creatinine and BUN, and it can be inferred that renal failure can be easily and early diagnosed only with urine without using blood. According to the diagnostic analysis of renal dysfunction caused by drug administration using a conventional indicator, renal dysfunction can be predicted to some extent, but as known in the art, renal dysfunction occurs after renal tissue is considerably damaged, and thus it is difficult to sensitively predict renal dysfunction in an early stage due to very low sensitivity and specificity of markers (BUN and creatinine) for renal dysfunction. Therefore, when SBP1 is used as an indicator, that is, a marker, for diagnosing a kidney disease, it can be seen that renal dysfunction induced by a drug can be effectively diagnosed in an early stage due to excellent sensitivity and specificity.

Example 4. Measurement of Urinary SBP1 Level in Hepatotoxicity Model

To confirm whether urinary SBP1 is released in a hepatotoxicity model, a hepatotoxic material such as carbon tetrachloride ($CCl_4$) was administered to a rat to induce hepatotoxicity, and then SBP1 level in urine was measured.

Figure 9A:
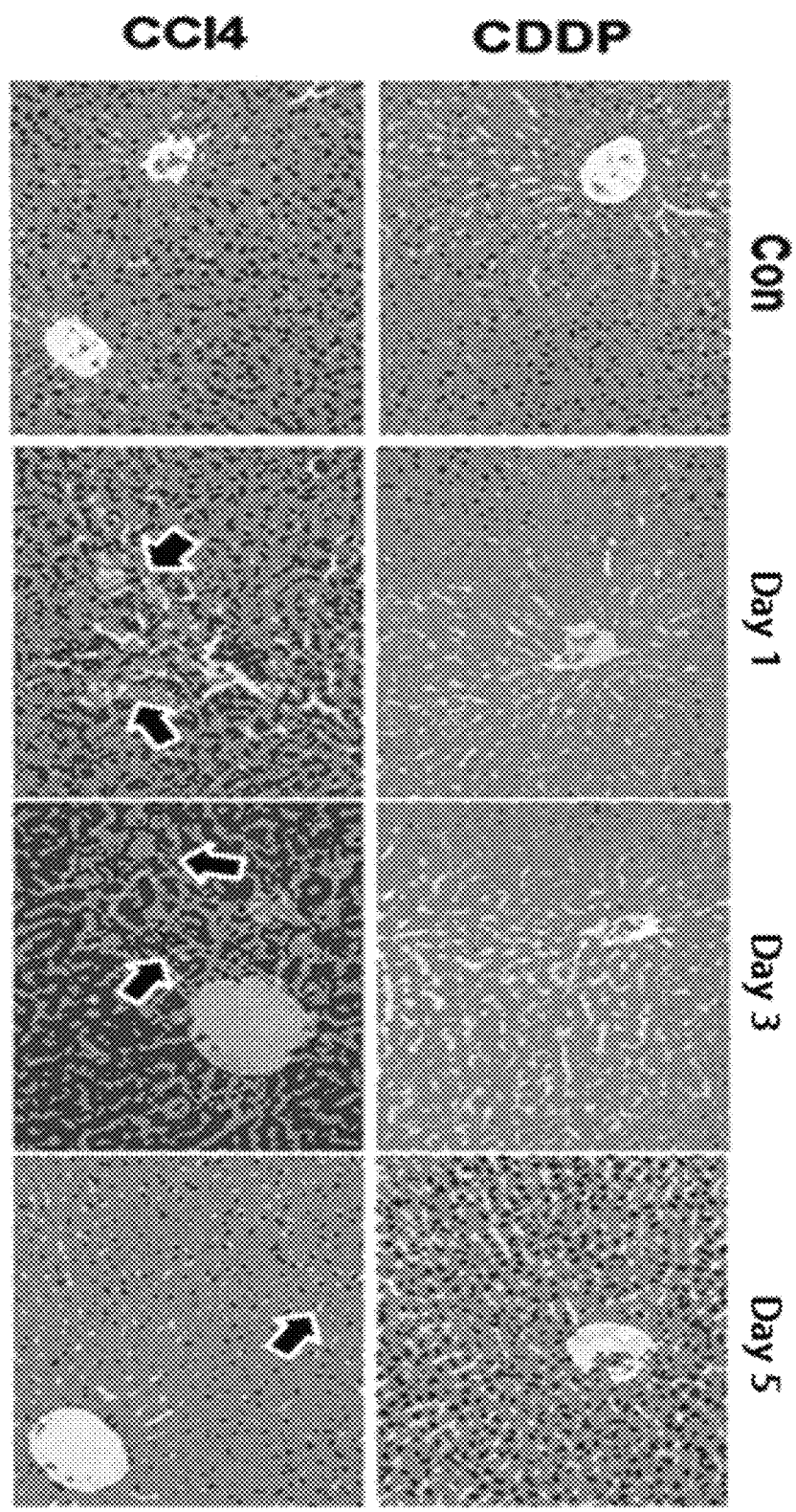
FIG. 9A shows a histopathological result obtained by H&E staining of the liver of a rat to which cisplatin and carbon tetrachloride ($CCl_4$) are administered.
Figure 9B:
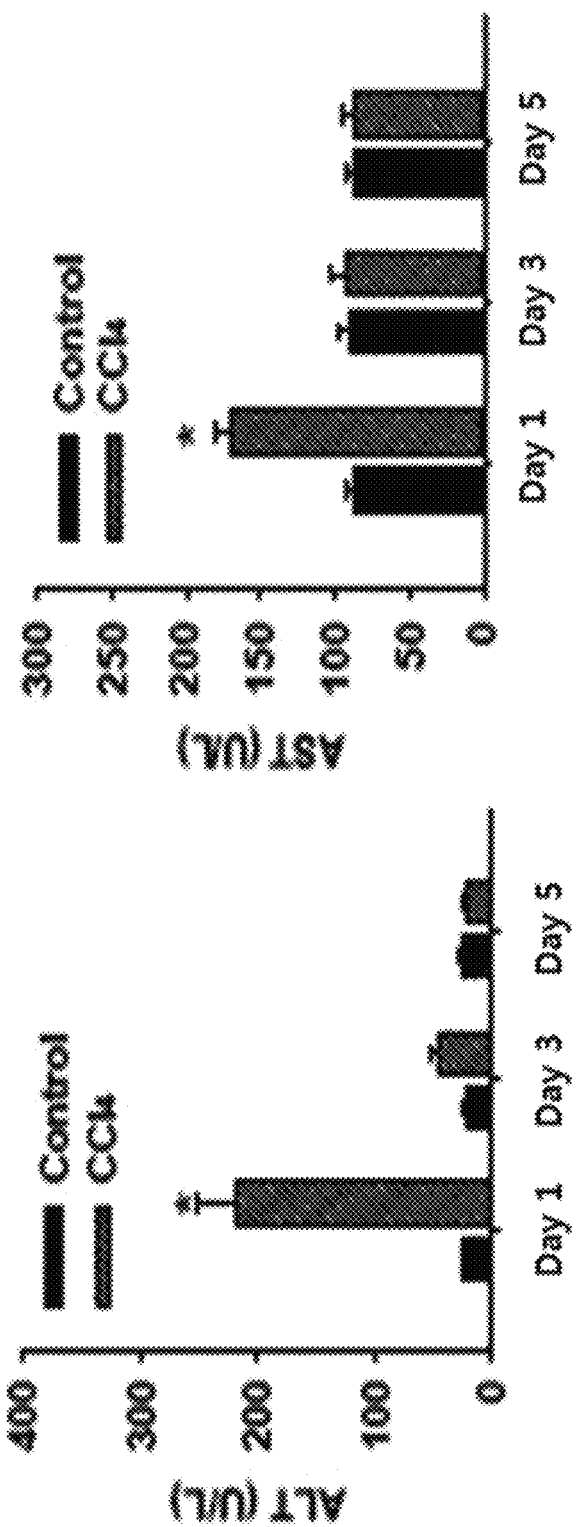
FIG. 9B shows a result of confirming AST and ALT levels, which are hepatoxicity indicators, by time, for example, on Day 1, 3 and 5 after administration of $CCl_4$.

As a result, as shown in FIG. 9A, histopathological findings obtained by H&E staining for the liver of a carbon tetrachloride-administered rat indicated that hepatotoxicity was not induced in a cisplatin-administered group, but severe liver failure was observed from one day after administration in the carbon tetrachloride-administered group and gradually recovered over time. In addition, as shown in FIG. 9B, it can be confirmed that, hepatotoxicity indicators, AST and ALT levels, were increased one day after administration and then decreased in the carbon tetrachloride-administered group, compared with the control.

Figure 9C:
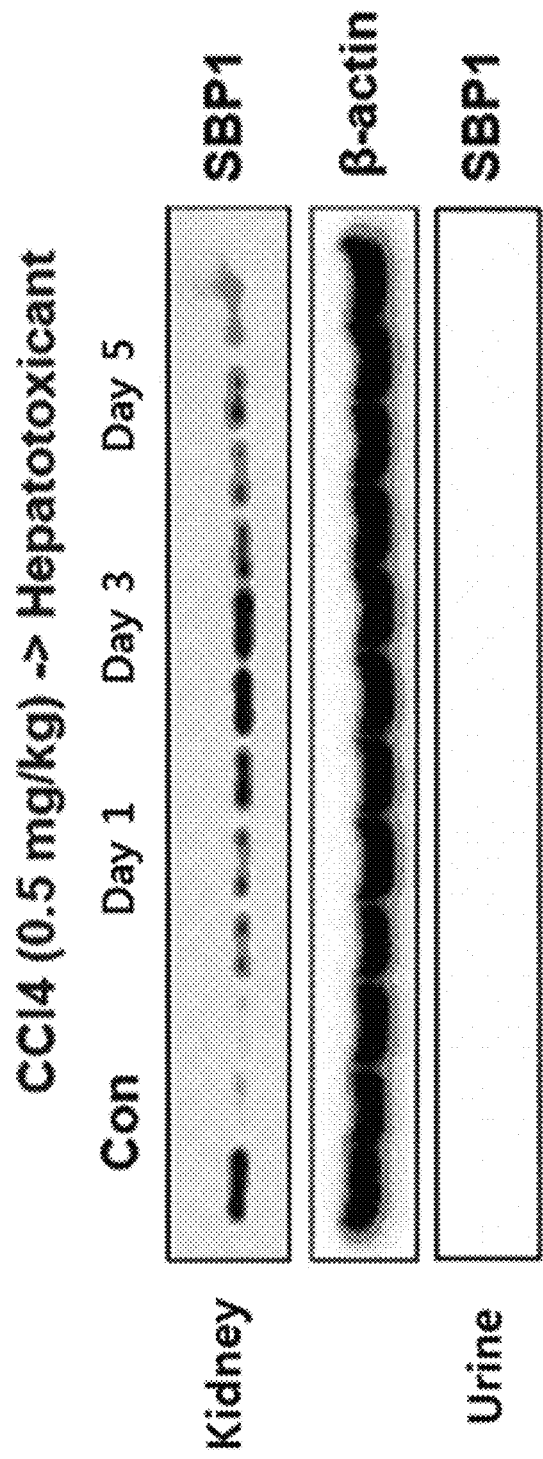
FIG. 9C shows a quantification result through western blotting to see whether SBP1 is generated by administration of a hepatoxic material in urine.
Figure 9D:
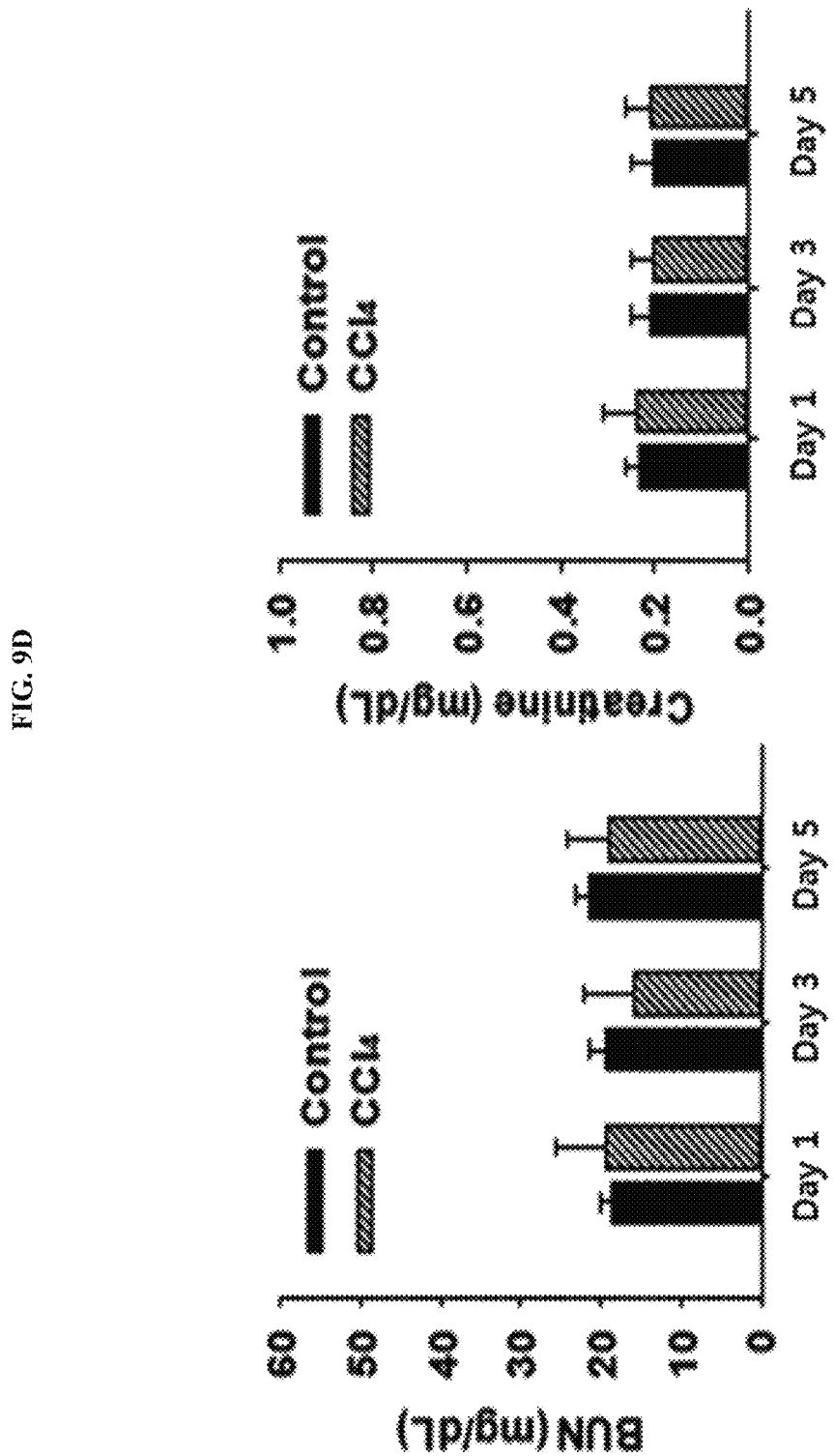
FIG. 9D is a result of confirming changes in BUN and creatinine levels, which are nephrotoxic indicators, according to administration of a hepatoxic material.

Moreover, as a result of western blotting, as shown in FIG. 9C, SBP1 was not detected in urine when a hepatotoxic material was administered, and as shown in FIG. 9D, it can be confirmed that there are no changes in nephrotoxicity indicators BUN and creatinine.

From the above result, it can be inferred that SBP1 is nephrotoxicitiy-specifically detected in urine. In other words, it can be seen that SBP1 has a very high specificity associated with a kidney disease.

Figure 10A:
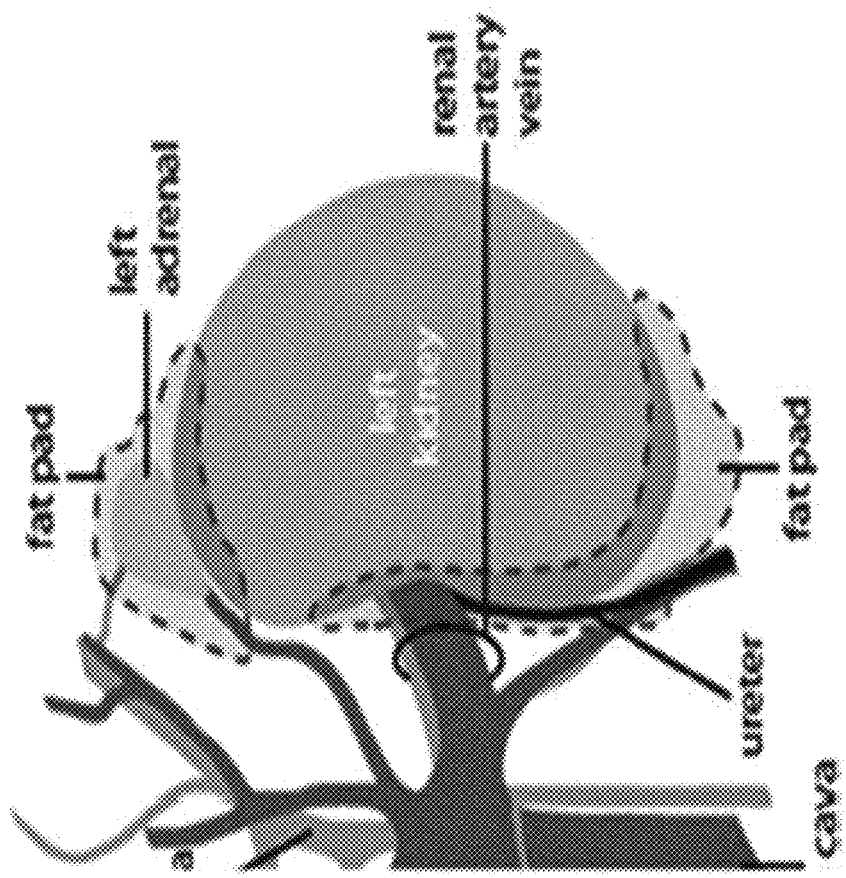
FIG. 10A shows the design of an ischemic kidney disease (ischemia/reperfusion) model as a test model for inducing acute renal failure.

Example 5. Measurement of Urinary SBP1 Level in Ischemia/Reperfusion Model 5-1. Preparation of Ischemia/Reperfusion Model First, it is preferable to accurately display a kidney location for incision. Incision should be performed by minimal scissoring, rather than scissoring several times. This is because when the cut surface is smooth, it is easy to suture later, and reduce time. The outer skin is cut along the incision line, the middle layer between the outer skin and the inner skin was removed well, and then the inner skin was incised. The kidney was carefully removed with forceps. Here, care is needed to prevent damage to the kidney, and when it is difficult to pick up the kidney, it is helpful to pull the kidney out of the fat layer. Almost all of the peripheral fat layer was removed to clearly see the hillum of the kidney (where kidney vessels gather), and the hillum of the kidney was tightly tied by making several knots with a nylon string. Afterward, the kidney was removed by cutting the upper part of the knots (see FIG. 10A). Care is needed to remove fat because excessive fat removal results in bleeding in blood vessels.

Figure 10B:
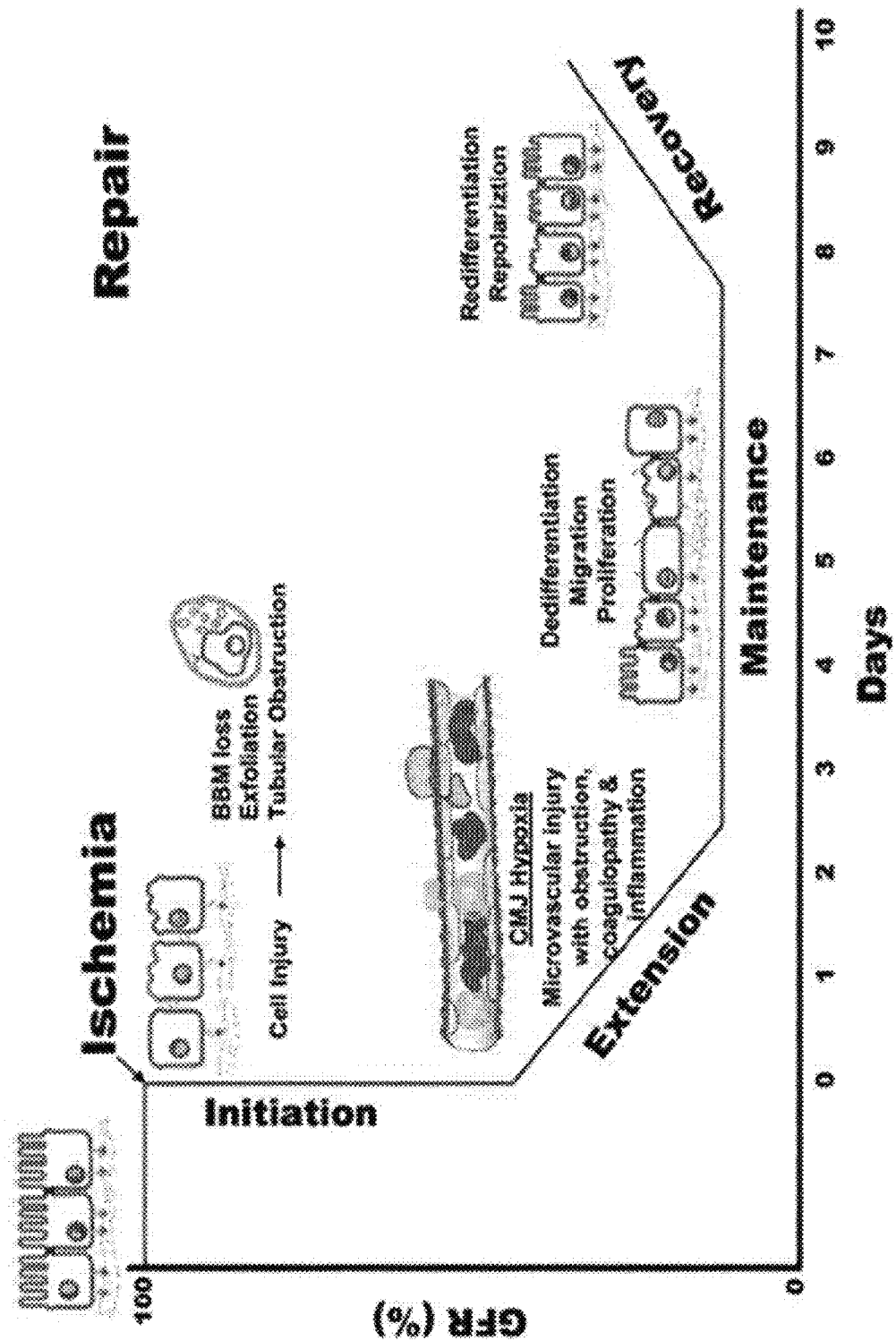
FIG. 10B shows the typical mechanism of ischemic renal failure.

Therefore, rats subjected to surgery were put into previously assembled metabolic cages (cages for metabolite analysis), and after surgery, as shown in Table 1 below, urine was collected at every time by group. Afterward, the urine collected in the metabolic cage was centrifuged at 3000 rpm for 10 minutes to precipitate impurities, and only a supernatant was obtained and dispensed into tubes which were previously named, followed by storage in a freezer. Here, the typical mechanisms of an ischemic kidney disease are shown in FIG. 10B.

TABLE 1

|  | Time of sacrifice | | |
| --- | --- | --- | --- |
| Pretreatment &IR | 9 hr | 24 hr | 48 hr |
| Group 1 (Sham) | Collected after 9 hr | Collected after 24 hr | Collected after 48 hr |
| Group 2 (IR) | Collected after 9 hr | Collected after 24 hr | Collected after 48 hr |

5-2. Measurement of SBP1 Level in Urine

Figure 11A:
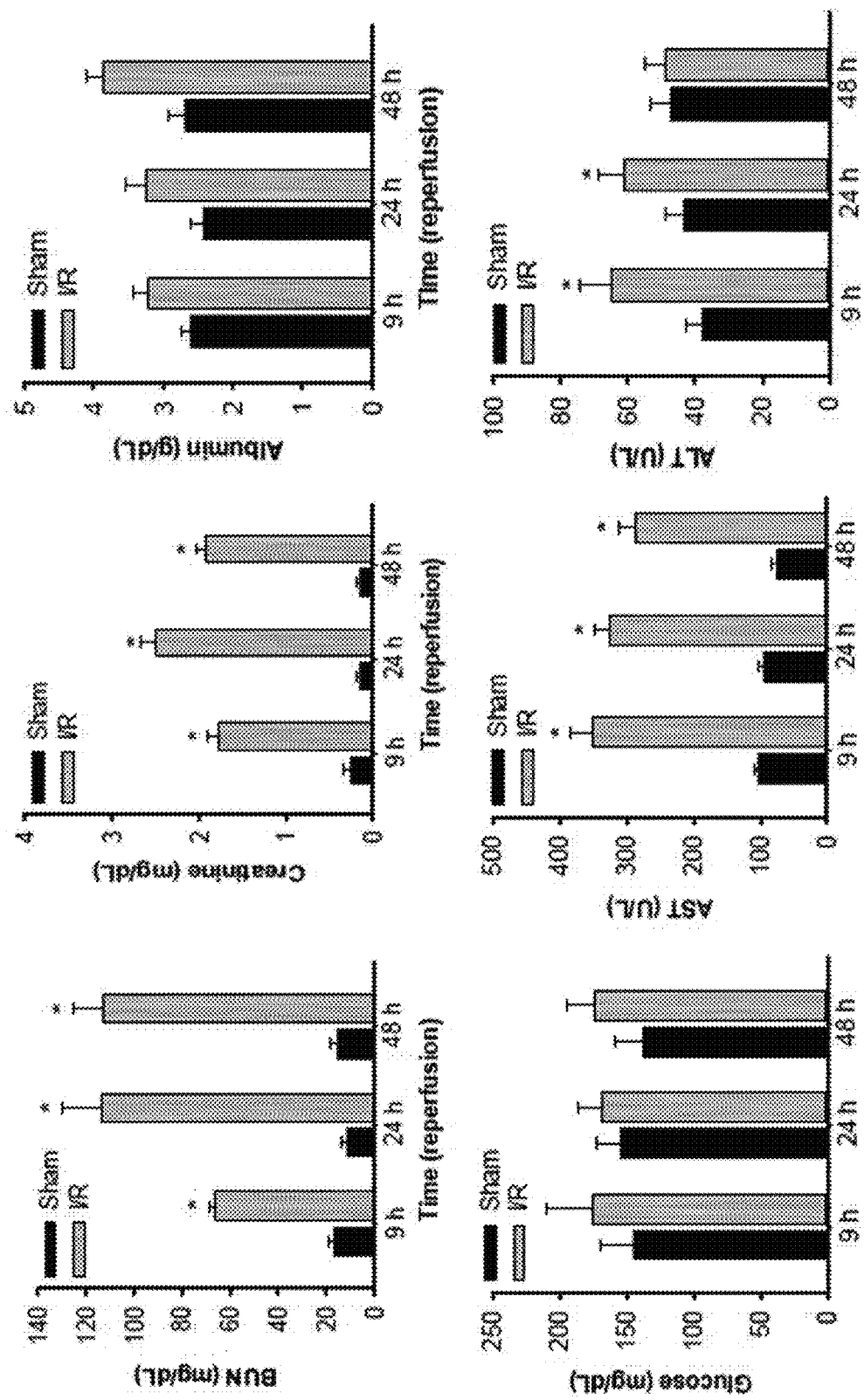
FIG. 11A shows a result of evaluating nephrotoxicity indicators by obtaining blood at 9, 24 and 48 hours after induction of ischemic renal failure.
Figure 11B:
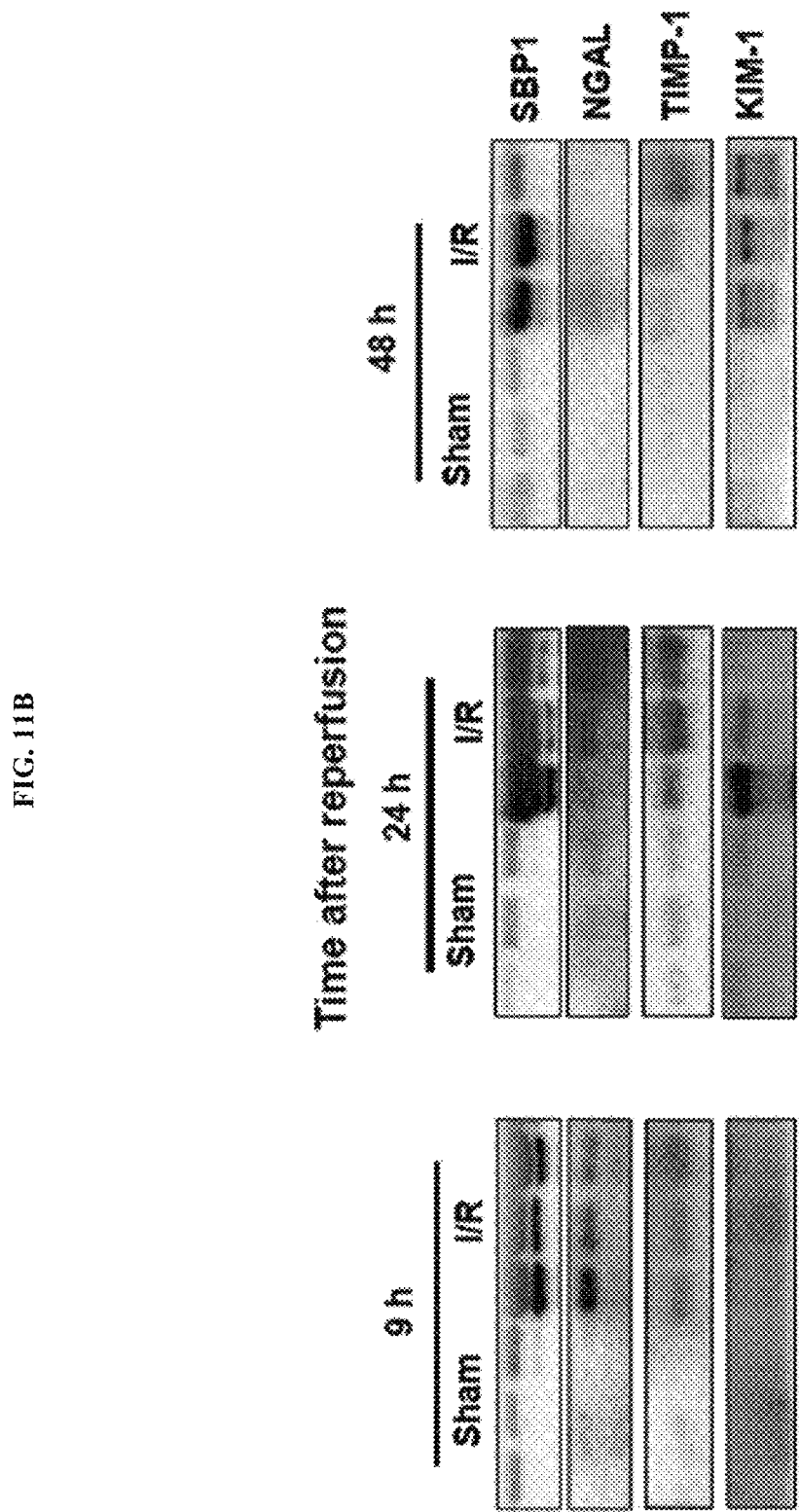
FIG. 11B shows a result of comparing urinary SBP1 and conventional biomarkers of renal dysfunction in an ischemia/reperfusion model and a Sham group (group in which surgery was not performed).

As shown in FIG. 11A, after ischemic renal failure was induced, blood samples were collected at 9 hours, 24 hours and 48 hours to evaluate nephrotoxicity, thereby confirming that BUN and creatinine levels were increased at all times. Compared with the sham group (group in which surgery was not performed), urinary SBP1 and the conventional renal dysfunction biomarkers were compared, and as a result of the comparison, as shown in FIG. 11B, through western blotting to quantify SBP1 released into urine, it was seen that SBP1 detected in the urine by IR is significantly increased.

The above result indicated that SBP1 can exhibit excellent sensitivity as a urinary diagnostic marker for ischemic acute renal failure.

Example 6. Measurement of Urinary SBP1 Level in Acute Renal Failure Patient 6-1. Collection and Analysis Method of Samples (Urine)

Subsequently, SBP1 levels were measured in urine samples of an acute renal failure patient group (P1~P7) and urine samples of a normal group (C1~05), respectively. The urine samples obtained from the acute renal failure patients were provided by the Medical School of Korea University (urine samples prior to IRB approval) to be used for experiments, and SBP1, KMI-1, NGAL and TIMP-1 contents in urine were analyzed according to Example 1-3 using antibodies specifically reacting with the above proteins.

6-2. Measurement of Urinary Protein Contents

Figure 12A:
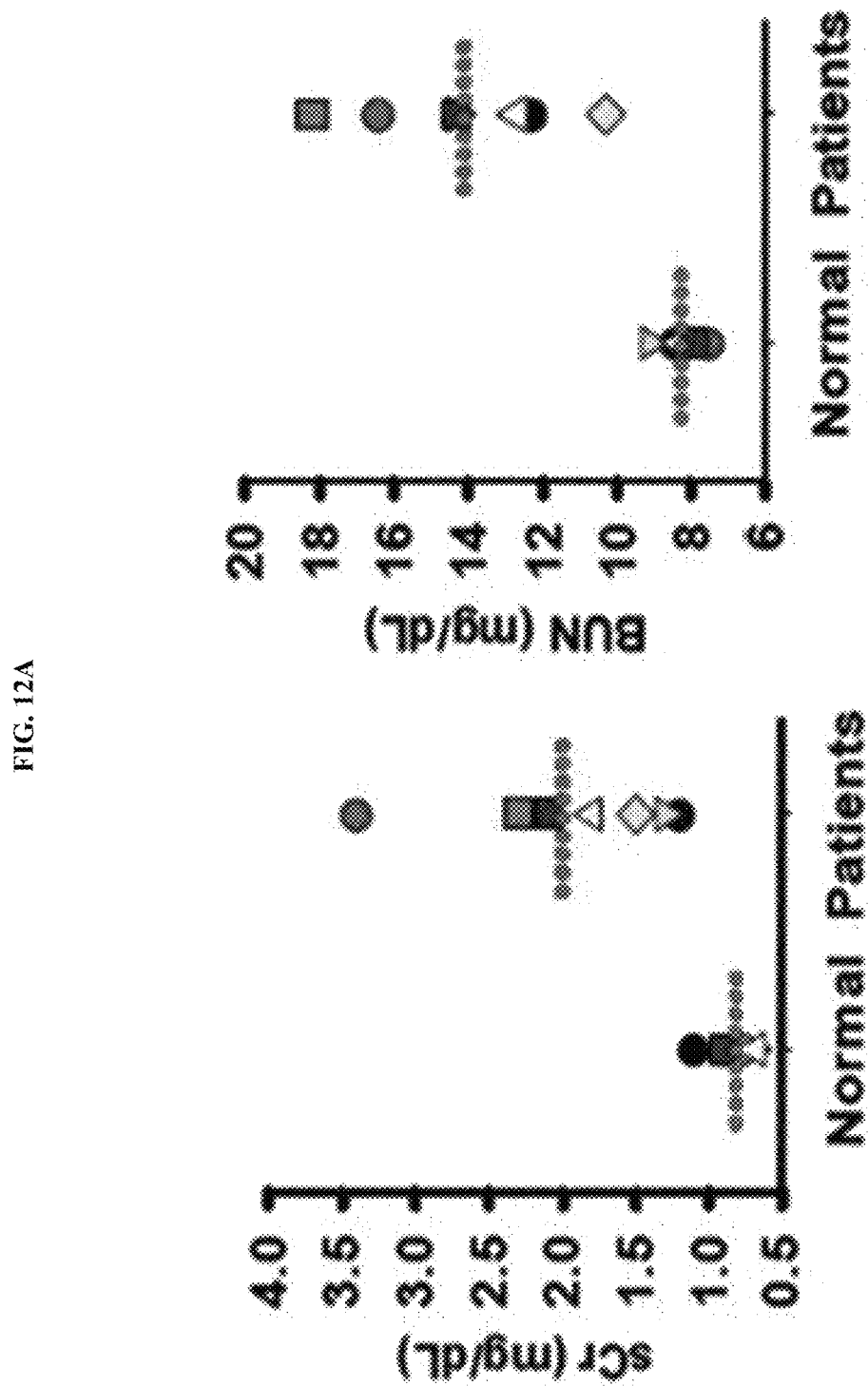
FIG. 12A shows the comparison of BUN and creatinine contents in normal patients and renal failure patients.

As a result, as shown in FIG. 12A, first, BUN and creatinine levels in acute renal failure patients and normal persons were measured, and it was confirmed that the renal failure patients showed increases in levels of these nephrotoxicity indicators.

Figure 12B:
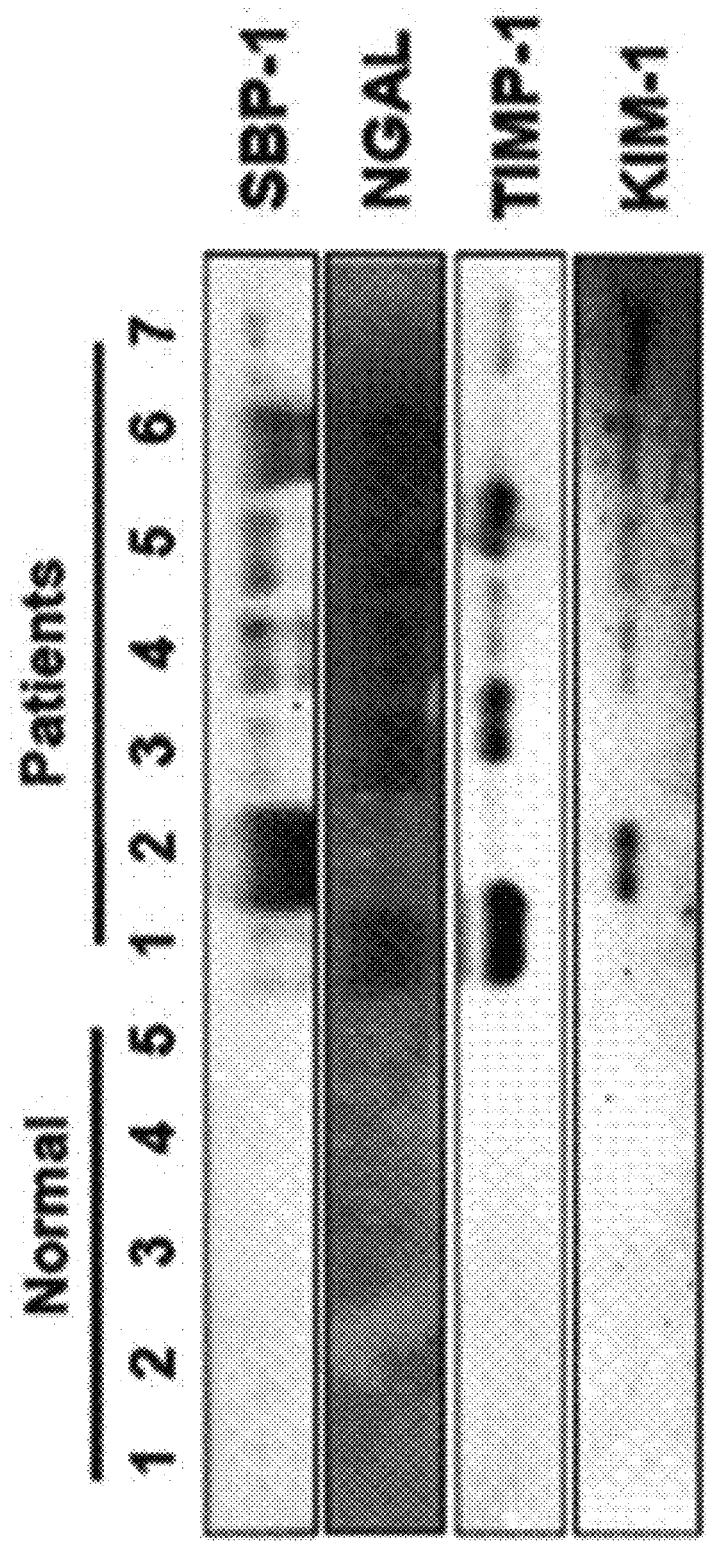
FIG. 12B shows a result of measuring SBP1, NGAL, TIMP1 and KIM-1 contents in urine through western blotting.

In addition, as shown in FIG. 12B, it was confirmed that SBP1 is highly elevated in the urine of an acute renal failure patient.

Like the animal test result, the above result demonstrates that, also in clinical samples, urinary SBP1 was not detected in normal persons, but only detected in renal failure patients.

In addition, BUN, blood creatinine and urinary SBP1 were measured for 20 patients admitted to the ICU.

More specifically, there was no information on who in the patient groups has renal failure, and it has been reported that approximately 50% or more of the patients admitted to the ICU generally have renal failure, and thus the occurrence of renal failure was evaluated in the present invention.

Figure 13:
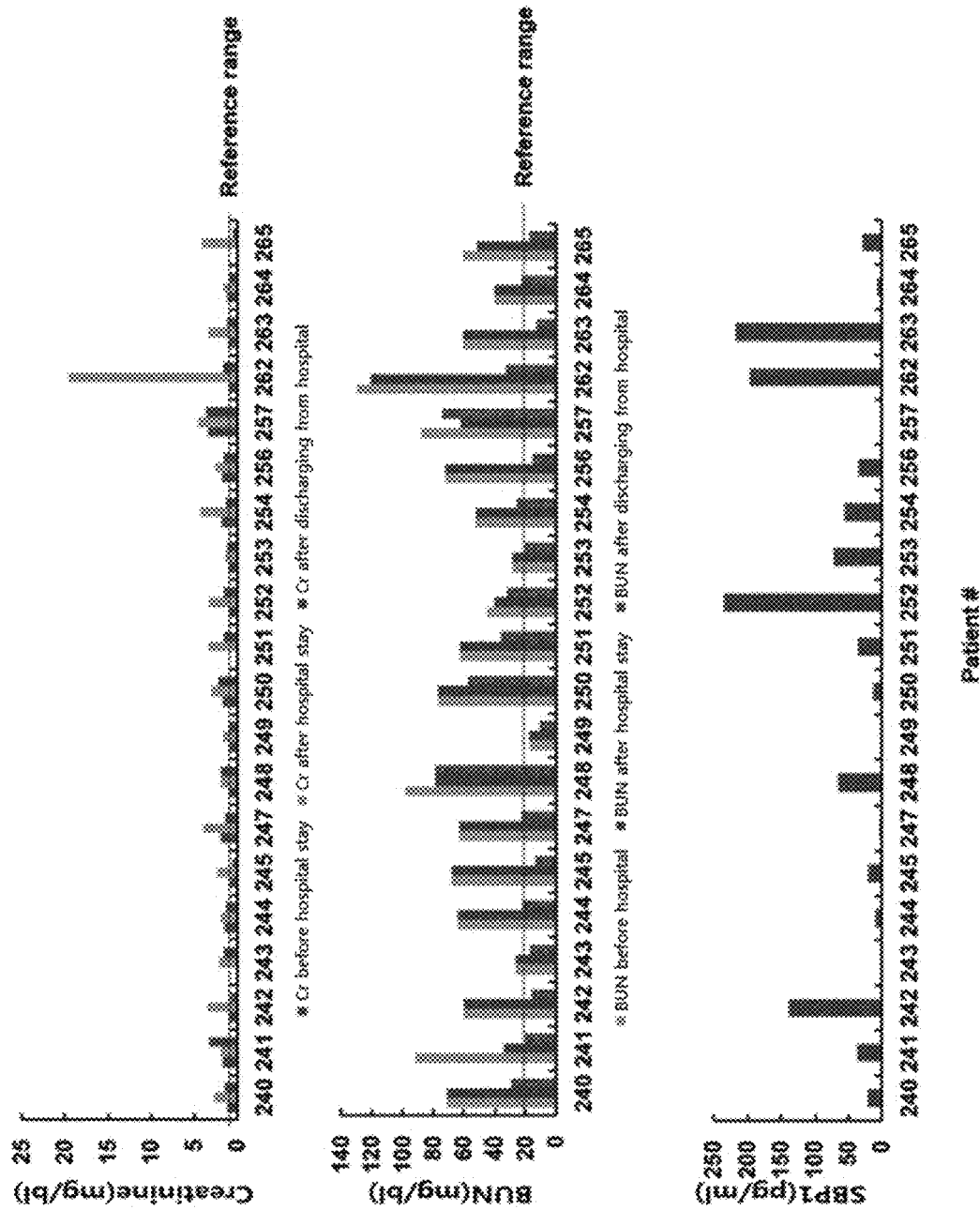
FIG. 13 shows a result of measuring BUN, creatinine and SBP1 in urine for 20 patients admitted to the ICU.

As a result, as shown in FIG. 13, in most patients, high creatinine levels were detected before hospitalization, and after hospitalization, some patients showed improved effects. Therefore, urinary SBP1 was highly detected in approximately 70% or more of the patients. Particularly, it was shown that, in patient no. 262, a very high blood creatinine level and a high level of SBP1 were detected.

6-3. Receiver Operating Characteristic Curve (ROC)-Area Under Curve (AUC) Analysis Based on the above result, to determine sensitivity and specificity of a method of diagnosing renal dysfunction using SBP1, ROC-AUC parameter analysis for each marker on drug-induced renal dysfunction was performed according to a conventional method (the ROC-AUC analysis conventionally shows that when the AUC value is 0.7 or more, it is determined that the marker has significance, and when the AUC value is closed to 1, it is determined that the marker is excellent).

Figure 14:
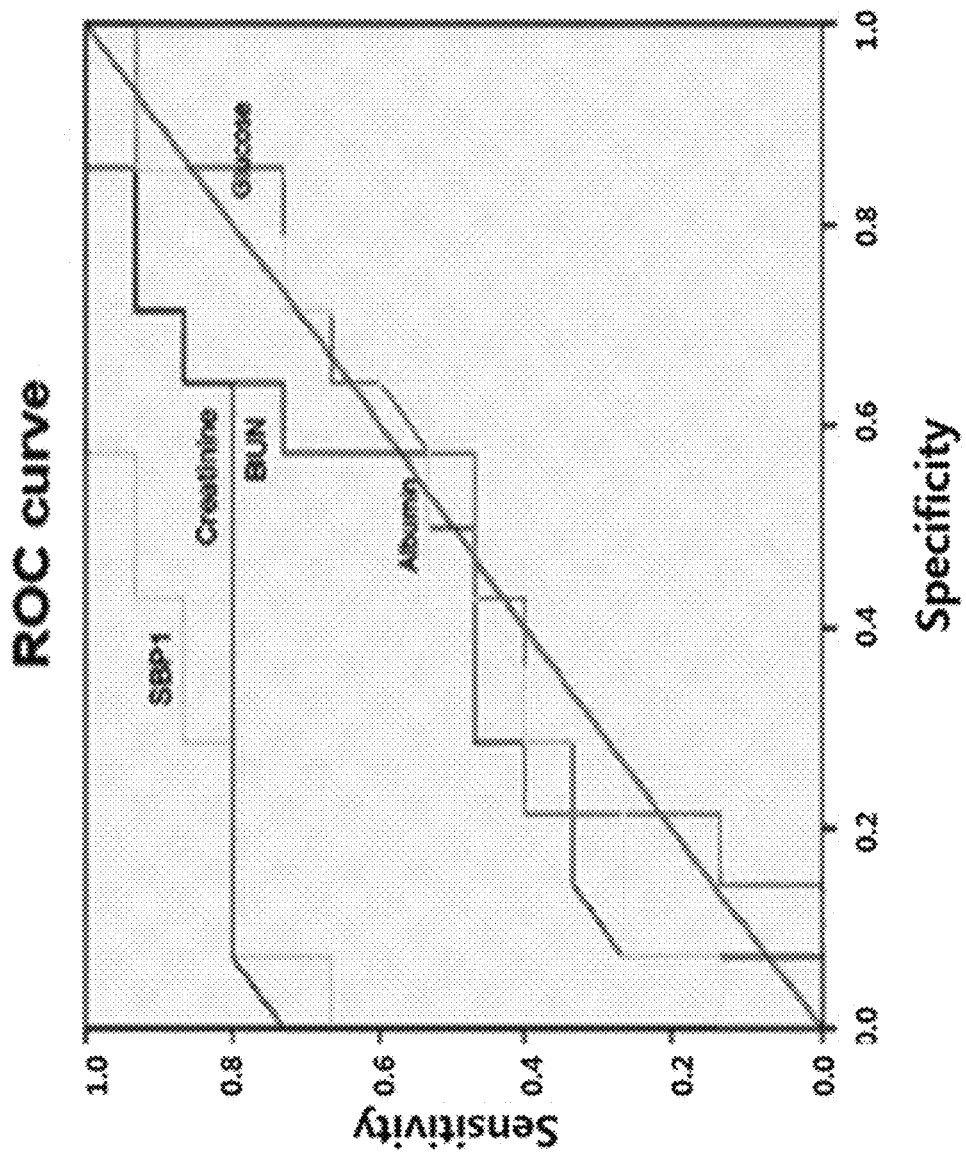
FIG. 14 shows a result of a receiver operating characteristic curve (ROC)-area under curve (AUC) parameter analysis for drug-induced renal dysfunction by each marker in urine.

As shown in FIG. 14, as a result of analyzing a method of diagnosing renal dysfunction in a clinical sample using SBP1 as an indicator, it was confirmed that SBP1 showed itself to be an excellent parameter having an AUC value (0.98) close to 1, and the SBP1 of the present invention exhibits considerably excellent sensitivity and specificity for renal dysfunction as compared with conventional renal dysfunction markers.

Example 7. Measurement of Kidney Disease-Associated Protein Contents in Urine

Figure 15:
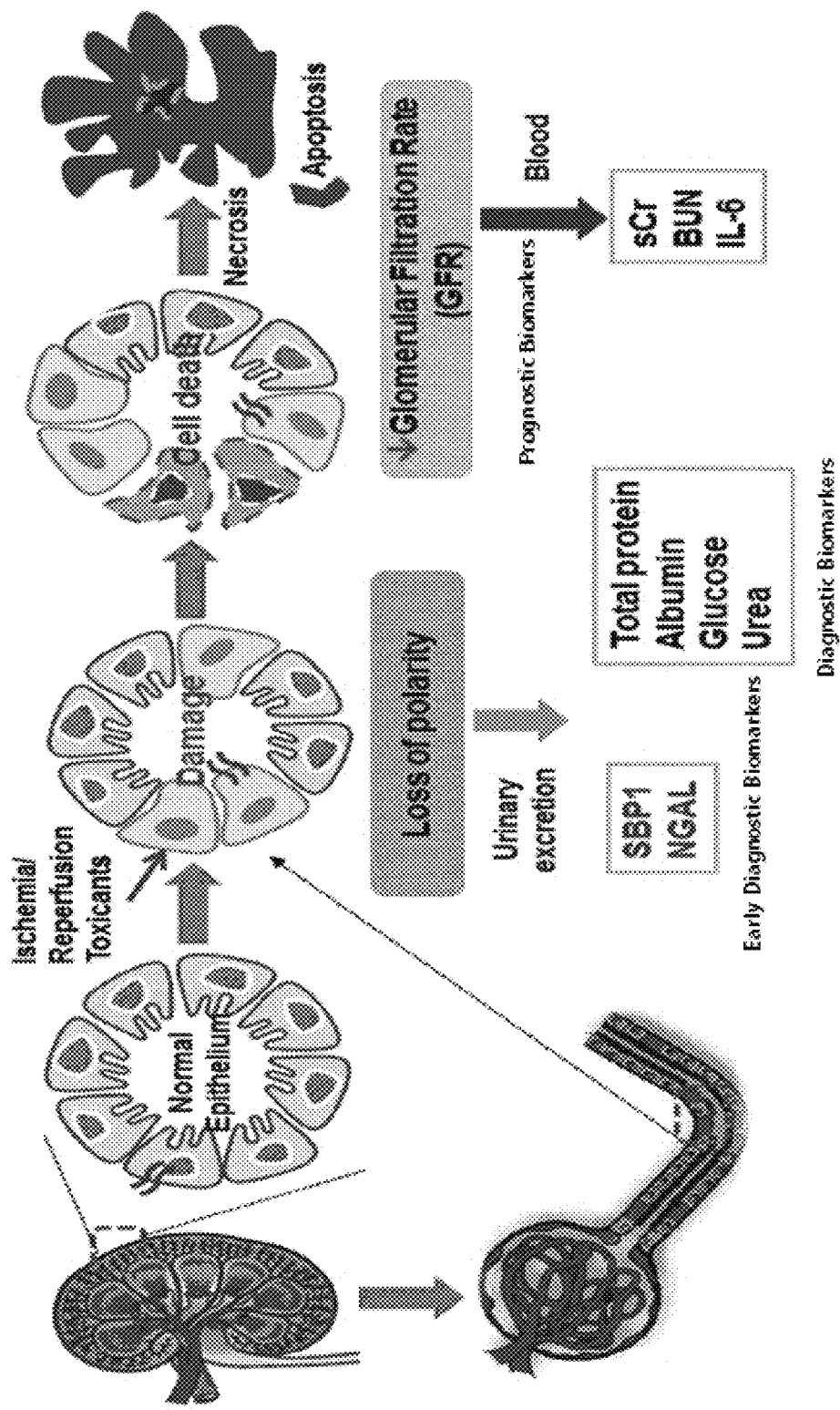
FIG. 15 illustrates the types of biomarkers for diagnosing the deterioration of renal function, which are known to date.

While KIM-1 and NGAL have been used clinically as renal dysfunction biomarkers in urine (see FIG. 15), since these biomarkers are expensive for clinical use, they are not easily used. Nevertheless, many researchers use KIM-1 and NGAL as biomarkers for detecting renal failure.

Accordingly, in the present invention, urinary contents of SBP1, KMI-1, NGAL and TIMP-1 were analyzed using antibodies specifically reacting with the proteins according to the method described in Example 1-3.

More specifically, in animal models in which diabetes is induced by STZ administration, when nephrotoxicity is induced, an SBP1 level detected in urine was measured using western blotting (antigen-antibody reaction). Likewise, SBP1 levels in animal models with diabetes induced by a high fat diet, ZDF rats, were measured using western blotting (antigen-antibody reaction).

As a result, as shown in FIG. 4E, it can be confirmed that SBP1 was not detected in the normal group at all, but SBP1 was increased 2 months after administration in a time-dependent manner, and here, recently reported diagnostic biomarkers of renal failure, such as NGAL and KIM-1, were increased 4 months after administration. Accordingly, it can be seen that for diabetic renal failure, SBP1 has a higher sensitivity than different types of diagnostic markers, demonstrating that SBP1 is excellent as an early diagnostic biomarker.

In addition, as shown in FIG. 8C, as a result of comparing urinary SBP1 levels in the cisplatin-administered experimental group and the non-treated control, urinary SBP1 levels are highly increased in the renal dysfunction-induced experimental group on Day 3, compared with the control, and particularly, such increase in SBP1 level is considerably shown from Day 3, which is the third day after drug administration.

Taken the above results together, it was expected that no SBP1 was detected in normal urine, and that renal tubular cells are damaged in the early stage of renal dysfunction and detected in urine, and generally, it can be seen that SBP1 is increased in the early stage as a prevention mechanism when oxidative damage to tissue is induced in kidney cells, and cells are disrupted, SBP1 is released outside the cells and excreted into urine when oxidative damage is severe. When SBP1 is used as an indicator for diagnosing a kidney disease, that is, a urinary marker, it can be seen that drug-induced renal dysfunction can be very rapidly, simply and effectively diagnosed in its early stage due to excellent sensitivity and specificity.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

The present invention relates to technology capable of early diagnosis of a kidney disease by measuring an SBP1 expression level in urine, and since the method for early diagnosis of a kidney disease according to the present invention is simple, and has high sensitivity and specificity, SBP 1 can be widely used in various fields such as diagnosis of drug-induced acute renal failure which can frequently occur in clinical treatment, and a preclinical toxicity test which is essential for the development of a new drug.

The invention claimed is:

1. A method for diagnosis and treatment of diabetic kidney disease in a human subject, which comprises:
   a) detecting an elevated level of Selenium-Binding Protein 1 (SBP1) in a urine sample of said subject relative to a control sample using an antibody specific to SBP1, thereby diagnosing said subject with diabetic kidney disease; and
   b) administering a therapy for diabetic kidney disease to the subject, wherein said therapy comprises one or more selected from the group consisting of: a therapy to reduce high blood pressure, a therapy to reduce hyperlipidemia, a therapy to reduce hyperglycemia, diet, and exercise.

2. The method according to claim 1, further comprising: detecting serum creatinine (SCr), blood urea nitrogen (BUN), glucose contained in urine, LDH, aspartate aminotransferase (AST) or total protein in a sample of a subject.

3. The method according to claim 1, further comprising: detecting KMI-1, NGAL or TIMP-1 in a sample of a subject.

* * * * *

SEQUENCE LISTING

```
<160> NUMBER OF SEQ ID NOS: 1

<210> SEQ ID NO 1
<211> LENGTH: 664
<212> TYPE: PRT
<213> ORGANISM: Artificial Sequence
<220> FEATURE:
<223> OTHER INFORMATION: Selenium-Binding Protein 1 (SBP1)

<400> SEQUENCE: 1

Ala Thr Gly Cys Cys Ala Ala Cys Ala Gly Gly Cys Cys Thr Gly Gly
1               5                   10                  15

Thr Cys Ala Gly Gly Cys Cys Gly Cys Cys Thr Gly Gly Cys Ala Cys
                20                  25                  30

Cys Thr Thr Cys Cys Thr Cys Cys Ala Thr Gly Gly Gly Thr Gly
            35                  40                  45

Cys Thr Gly Thr Gly Gly Ala Ala Gly Ala Gly Cys Thr Thr Gly Gly
        50                  55                  60

Cys Ala Cys Cys Cys Gly Thr Cys Thr Thr Cys Cys Cys Cys Thr Gly
65                  70                  75                  80

Thr Gly Gly Gly Cys Cys Cys Ala Gly Cys Thr Gly Cys Thr Ala Thr
                85                  90                  95

Thr Cys Gly Gly Cys Ala Cys Thr Gly Gly Cys Gly Gly Cys Gly Gly
            100                 105                 110

Gly Cys Cys Ala Gly Gly Gly Cys Cys Cys Thr Cys Gly Gly Gly
        115                 120                 125

Gly Thr Gly Cys Thr Thr Thr Ala Ala Gly Gly Ala Thr Gly Thr Cys
    130                 135                 140

Gly Ala Thr Gly Thr Cys Ala Gly Cys Ala Cys Cys Ala Ala Ala Cys
145                 150                 155                 160

Cys Cys Thr Thr Gly Thr Cys Thr Cys Ala Ala Thr Ala Gly
                165                 170                 175

Cys Gly Thr Gly Thr Cys Ala Cys Ala Ala Cys Cys Thr Gly
            180                 185                 190

Gly Ala Thr Thr Thr Gly Ala Thr Gly Cys Ala Gly Cys Thr Gly Gly
```

-continued

```
            195                 200                 205
Gly Ala Ala Cys Cys Ala Gly Cys Cys Ala Cys Thr Ala Ala
    210                 215                 220
Cys Ala Gly Ala Gly Gly Cys Thr Gly Cys Cys Thr Cys Ala Thr Cys
225                 230                 235                 240
Thr Thr Cys Ala Thr Gly Cys Ala Gly Cys Ala Cys Thr Gly Cys
                245                 250                 255
Cys Ala Gly Ala Thr Gly Cys Ala Gly Ala Gly Ala Gly Gly Ala
                260                 265                 270
Thr Gly Thr Cys Thr Ala Gly Gly Cys Ala Ala Gly Ala Gly Gly
        275                 280                 285
Cys Cys Thr Ala Ala Cys Thr Cys Cys Cys Ala Gly
        290                 295                 300
Cys Thr Cys Cys Ala Gly Thr Gly Ala Thr Gly Gly Gly Ala Thr
305                 310                 315                 320
Cys Cys Cys Cys Thr Cys Ala Ala Gly Gly Ala Cys Cys Thr Ala
                325                 330                 335
Cys Cys Thr Gly Gly Cys Ala Gly Cys Thr Gly Thr Cys Ala Gly Ala
            340                 345                 350
Gly Gly Ala Ala Gly Gly Gly Ala Thr Gly Ala Gly Ala Gly Ala
            355                 360                 365
Cys Ala Gly Ala Gly Gly Cys Cys Cys Ala Cys Cys Ala Cys
    370                 375                 380
Cys Cys Thr Gly Thr Ala Cys Thr Ala Ala Gly Thr Thr Thr Cys
385                 390                 395                 400
Cys Ala Cys Thr Thr Gly Gly Cys Cys Thr Thr Gly Thr Cys Thr Thr
                405                 410                 415
Thr Ala Gly Thr Gly Gly Cys Cys Ala Ala Gly Gly Cys Ala Gly
            420                 425                 430
Gly Gly Gly Thr Thr Gly Thr Cys Ala Ala Cys Cys Cys Ala Gly
            435                 440                 445
Thr Cys Thr Gly Ala Cys Thr Thr Gly Cys Cys Ala Thr Gly Cys Ala
        450                 455                 460
Gly Gly Gly Gly Ala Gly Ala Gly Thr Gly Gly Thr Thr Thr Gly
465                 470                 475                 480
Gly Cys Ala Cys Cys Thr Gly Cys Cys Thr Thr Cys Thr Cys Ala Thr
                485                 490                 495
Cys Cys Ala Gly Gly Cys Cys Cys Ala Gly Gly Cys Cys Ala Gly
            500                 505                 510
Ala Gly Gly Cys Cys Ala Gly Thr Gly Gly Gly Gly Ala Ala Gly Ala
        515                 520                 525
Ala Gly Gly Gly Thr Gly Gly Gly Thr Cys Ala Asn Gly Ala Ala Ala
        530                 535                 540
Gly Gly Ala Thr Gly Ala Ala Asn Gly Cys Ala Gly Gly Cys Ala Gly
545                 550                 555                 560
Gly Gly Ala Cys Thr Gly Cys Cys Cys Ala Ala Gly Gly Gly Ala Thr
            565                 570                 575
Ala Gly Ala Ala Cys Cys Cys Ala Ala Gly Gly Thr Gly Gly Cys
            580                 585                 590
Cys Thr Thr Gly Gly Gly Ala Thr Cys Ala Ala Gly Cys Gly Gly
        595                 600                 605
Gly Gly Thr Gly Cys Ala Cys Ala Cys Cys Cys Thr Gly Cys Thr Thr
610                 615                 620
```

```
Cys Cys Thr Thr Gly Ala Gly Cys Cys Thr Cys Gly Thr Thr Gly Ala
625                 630             635                 640

Ala Cys Thr Thr Gly Gly Cys Ala Ala Gly Thr Gly Ala Ala Asn
                645             650                 655

Gly Thr Gly Gly Gly Ala Ala Thr
                660
```